United States Patent
Winston

(10) Patent No.: US 11,931,459 B2
(45) Date of Patent: Mar. 19, 2024

(54) TREATMENT OF PAIN IN PEDIATRIC PATIENTS BY ADMINISTRATION OF SUSTAINED-RELEASE LIPOSOMAL ANESTHETIC COMPOSITIONS

(71) Applicant: Pacira Pharmaceuticals, Inc., Parsippany, NJ (US)

(72) Inventor: Roy Winston, Parsippany, NJ (US)

(73) Assignee: Pacira Pharmaceuticals, Inc., Parsippany, NJ (US)

( * ) Notice: Subject to any disclaimer, the term of this patent is extended or adjusted under 35 U.S.C. 154(b) by 0 days.

(21) Appl. No.: 17/697,261

(22) Filed: Mar. 17, 2022

(65) Prior Publication Data

US 2022/0387318 A1 Dec. 8, 2022

Related U.S. Application Data

(60) Provisional application No. 63/163,672, filed on Mar. 19, 2021.

(51) Int. Cl.
*A61K 9/127* (2006.01)
*A61K 9/107* (2006.01)
*A61K 31/4375* (2006.01)
*A61K 31/66* (2006.01)

(52) U.S. Cl.
CPC ............ *A61K 9/1271* (2013.01); *A61K 9/107* (2013.01); *A61K 31/4375* (2013.01); *A61K 31/66* (2013.01)

(58) Field of Classification Search
None
See application file for complete search history.

(56) References Cited

U.S. PATENT DOCUMENTS

| | | | |
|---|---|---|---|
| 5,316,771 A | 5/1994 | Barenholz | |
| 5,817,074 A | 10/1998 | Racz | |
| 8,182,835 B2 | 5/2012 | Kim et al. | |
| 8,410,104 B2 | 4/2013 | Brummett | |
| 8,834,921 B2 | 9/2014 | Kim et al. | |
| 8,906,966 B2 | 12/2014 | Sherwood et al. | |
| 8,957,779 B2 | 2/2015 | Wu et al. | |
| 8,975,268 B2 | 3/2015 | Berde et al. | |
| 8,975,281 B2 | 3/2015 | Berde et al. | |
| 9,192,575 B2 | 11/2015 | Kim et al. | |
| 9,205,052 B2 | 12/2015 | Kim et al. | |
| 9,585,838 B2 | 3/2017 | Hartounian et al. | |
| 10,398,648 B2 | 9/2019 | Schutt et al. | |
| 11,033,495 B1 | 1/2021 | Hall et al. | |
| 11,179,336 B1 | 11/2021 | Hall et al. | |
| 11,278,494 B1 | 3/2022 | Hall et al. | |
| 11,304,904 B1 | 4/2022 | Hall et al. | |
| 11,311,486 B1 | 4/2022 | Hall et al. | |
| 11,357,727 B1 | 6/2022 | Hall et al. | |
| 11,426,348 B2 | 8/2022 | Hall et al. | |
| 11,452,691 B1 | 9/2022 | Hall et al. | |
| 11,759,459 B2 | 9/2023 | Winston et al. | |
| 11,812,358 B2 | 11/2023 | Slonin et al. | |
| 11,819,572 B2 | 11/2023 | Los et al. | |
| 11,819,573 B2 | 11/2023 | Slonin et al. | |
| 2002/0039596 A1 | 4/2002 | Hartounian et al. | |
| 2003/0059462 A1 | 3/2003 | Barenholz | |
| 2003/0069318 A1 | 4/2003 | Dang et al. | |
| 2003/0170288 A1 | 9/2003 | Carr et al. | |
| 2006/0078606 A1* | 4/2006 | Kim | A61K 31/167 424/450 |
| 2007/0249681 A1 | 10/2007 | Sudo et al. | |
| 2009/0105693 A1 | 4/2009 | Ben-David et al. | |
| 2009/0202436 A1 | 8/2009 | Hobot et al. | |
| 2011/0250264 A1 | 10/2011 | Schutt et al. | |
| 2012/0179038 A1 | 6/2012 | Meurer et al. | |
| 2013/0177633 A1 | 7/2013 | Schutt et al. | |
| 2013/0177634 A1 | 7/2013 | Schutt et al. | |
| 2013/0177635 A1 | 7/2013 | Schutt et al. | |
| 2013/0177636 A1 | 7/2013 | Schutt et al. | |
| 2013/0177637 A1 | 7/2013 | Schutt et al. | |
| 2013/0177638 A1 | 7/2013 | Schutt et al. | |
| 2013/0183372 A1 | 7/2013 | Schutt et al. | |
| 2013/0183373 A1 | 7/2013 | Schutt et al. | |
| 2013/0183375 A1 | 7/2013 | Schutt et al. | |
| 2013/0189349 A1 | 7/2013 | Kim et al. | |
| 2013/0195965 A1 | 8/2013 | Schutt et al. | |
| 2013/0306759 A1 | 11/2013 | Schutt et al. | |
| 2013/0344132 A1 | 12/2013 | Kim et al. | |
| 2014/0296293 A1 | 10/2014 | Andersen et al. | |
| 2015/0250724 A1 | 9/2015 | Yamashita et al. | |

(Continued)

FOREIGN PATENT DOCUMENTS

| | | |
|---|---|---|
| CN | 109745607 | 5/2019 |
| RU | 2307675 | 10/2007 |

(Continued)

OTHER PUBLICATIONS

Epstein et al (Anesthesiology, 69: 773-776, 1988). (Year: 1988).*
Stow et al (Anaesthesia, 1998, 43, 650-653). (Year: 1998).*
[No Author Listed] [online], "Full Prescribing Information—Exparel," exparel.com, revised Mar. 2022, retrieved on Apr. 14, 2022, retrieved from URL <https://www.exparel.com/hcp/prescribing-information.pdf?msclkid=60c82e5b2c231a2fdbe94c034f355fb2&utm_source=bing&utm_medium=cpc&utm_campaign=HCP%20-%20Branded&utm_term=exparel%20dosing%20information&utm_content=Dosage>, 36 pages.

(Continued)

*Primary Examiner* — Celeste A Roney
(74) *Attorney, Agent, or Firm* — Fish & Richardson P.C.

(57) ABSTRACT

In some embodiments provided herein is a method of treating pain, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

22 Claims, 4 Drawing Sheets

(56) References Cited

U.S. PATENT DOCUMENTS

| | | | |
|---|---|---|---|
| 2016/0000705 A1* | 1/2016 | McDonald | A61P 25/04 424/1.85 |
| 2016/0089335 A1 | 3/2016 | Ohri et al. | |
| 2016/0361260 A1 | 12/2016 | Schutt et al. | |
| 2016/0375140 A1 | 12/2016 | Ottoboni et al. | |
| 2017/0007549 A1 | 1/2017 | Yum et al. | |
| 2018/0092847 A1 | 4/2018 | Schutt et al. | |
| 2019/0231762 A1 | 8/2019 | Verity | |
| 2022/0015738 A1 | 1/2022 | Harbi et al. | |
| 2022/0096116 A1 | 3/2022 | McFarland et al. | |
| 2022/0273564 A1 | 5/2022 | Slonin et al. | |
| 2022/0218610 A1 | 7/2022 | Sionin | |
| 2022/0218613 A1 | 7/2022 | Slonin et al. | |
| 2023/0038098 A1 | 2/2023 | Winston et al. | |
| 2023/0042662 A1 | 2/2023 | Los et al. | |
| 2023/0052319 A1 | 2/2023 | Winston et al. | |
| 2023/0080593 A1 | 3/2023 | Winston et al. | |
| 2023/0087140 A1 | 3/2023 | Winston et al. | |
| 2023/0130180 A1 | 4/2023 | Los et al. | |

FOREIGN PATENT DOCUMENTS

| | | |
|---|---|---|
| WO | WO 1997/003652 | 2/1997 |
| WO | WO 1999/013865 | 3/1999 |
| WO | WO 1999/044640 | 9/1999 |
| WO | WO 2016/184661 | 11/2016 |
| WO | WO 2018/226732 | 12/2018 |
| WO | WO 2018/237109 | 12/2018 |
| WO | WO 2021/141956 | 7/2021 |
| WO | WO 2021/141959 | 7/2021 |
| WO | WO 2021/141963 | 7/2021 |

OTHER PUBLICATIONS

Ahiskalioglu et al., "Can high volume pericapsular nerve group (PENG) block act as a lumbar plexus block?" Journal of Clinical Anesthesia, May 2020, 61:109650, 2 pages.

Beachler et al. "Liposomal bupivacaine in total hip arthroplasty: Do the results justify the cost?" Journal of Orthopaedics, 2017, 14:161-165.

Biotechnology Innovation Organization "Re: Docket No. FDA-2019-N-2514: Standards for Future Opioid Analgesic Approvals and Incentives for New Therapeutics to Treat Pain and Addiction," Nov. 18, 2019, 11 pages.

Bronson et al. "Unanticipated transient sciatic nerve deficits from intra-wound liposomal bupivacaine injection during total hip arthroplasty," Arthroplasty Today, 2015, 1:21-24.

De Leeuw et al., "The Psoas Compartment Block for Hip Surgery: The Past, Present, and Future," Anesthesiology Research and Practice, 2011, Article ID 159541, pp. 1-6.

Duzlu et al., "Release Pattern of Liposomal Bupivacaine in Artificial Cerebrospinal Fluid," Turk J Anaesth Reanim., 2016, 44:1-6.

FDA.gov [online] "Methodologies for Determining Opioid Sparing in Acute Pain Models," available on or before Dec. 14, 2019, via Internet Archive: Wayback Machine URL <http://web.archive.org/web/20191214114348/https://www.fda.gov/media/121206/download>, 61 pages.

Ginosar et al., "ED50 and ED95 of Intrathecal Hyperbaric Bupivacaine Coadministered with Opioids for Cesarean Delivery," Anesthesiology, Mar. 2004, 100(3):676-682.

Giron Arango et al., "Reply to Dr Yu et al: Inadvertent quadriceps weakness following the pericapsular nerve group (PENG) block," Reg Anesth Pain Med, May 2019, 44(5):613-614.

Globalnewswire.com [online], "Pacira—EXPAREL Achieves Primary and Key Secondary Endpoints in Phase 4 CHOICE Study in Cesarean Section Patients," Jan. 7, 2020, retrieved on Apr. 11, 2022, retrieved from URL <https://www.globenewswire.com/news release/2020/01/07/1967140/0/en/EXPAREL-Achieves-Primary-and-Key-Secondary-Endpoints-in-Phase-4-CHOICE-Study-in-Cesarean-Section-Patients.html>, 6 pages.

Hadzic et al., "Liposome Bupivacaine Femoral Nerve Block for Postsurgical Analgesia after Total Knee Arthroplasty," Anesthesiology, Jun. 2016, 124(6):1372-1383.

International Preliminary Report on Patentability in International Appln. No. PCT/US2021/012266, dated Jul. 12, 2022, 14 pages.

International Preliminary Report on Patentability in International Appln. No. PCT/US2021/012269, dated Jul. 21, 2022, 23 pages.

International Preliminary Report on Patentability in International Appln. No. PCT/US2021/012275, dated Jul. 12, 2022, 13 pages.

International Search Report and Written Opinion in International Appln. No. PCT/US2021/012266, dated Apr. 30, 2021, 16 pages.

International Search Report and Written Opinion in International Appln. No. PCT/US2021/012269, dated Mar. 25, 2021, 25 pages.

International Search Report and Written Opinion in International Appln. No. PCT/US2021/012275, dated Mar. 25, 2021, 14 pages.

International Search Report and Written Opinion in International Appln. No. PCT/US2022/011828, dated Apr. 1, 2022, 18 pages.

Joshi et al., "The Safety of Liposome Bupivacaine Following Various Routes of Administration in Animals," Journal of Pain Research, 2015, 8:781-789.

Laura Giron-Arango et al., "Pericapsular Nerve Group (PENG) Block for Hip Fracture", Reg Anesth Pain Med, 2018, 43:859-863, 5 pages.

Malik et al., "Emerging roles of liposomal bupivacaine in anesthesia practice," Journal of Anaesthesiology Clinical Pharmacology, Apr. 0Jun. 2017, 33(2):151-156.

Malinovsky et al., "Neurotoxicological Assessment After Intracisternal Injection of Liposomal Bupivacaine in Rabbits," Anesth. Analg., 1997, 85:1331-1336.

Mannion et al., "In with the New, Out with the Old? Comparison of Two Approaches for Psoas Compartment Block," Anesthesia and Analgesia, 2005, 101:259-264.

Mannion, "Psoas Compartment Block," Continuing Education in Anesthesia, Critical Care & Pain, 2007, 7(5):162-166.

McGraw-Tatum et al. "A Prospective, Randomized Trial Comparing Liposomal Bupivacaine vs Fascia Iliaca Compartment Block for Postoperative Pain Control in Total Hip Arthroplasty," The Journal of Arthroplasty, 2017, 32:2181-2185.

Nedeljkovic et al., "Liposomal Bupivacaine Transversus Abdominis Plane Block for Pain After Cesarean Delivery: Results From a Multicenter, Randomized, Double-Blind, Controlled Trial," PowerPoint, Presented at Society for Obstetric Anesthesia and Perinatology 51st Annual Meeting, Phoenix, AZ, May 1-5, 2019, 17 pages.

Nedeljkovic et al., "Transversus Abdominis Plane Block With Liposomal Bupivacaine for Pain After Cesarean Delivery in a Multicenter, Randomized, Double-Blind, Controlled Trial," Anesth. Analg., Dec. 2020, 131(6):1830-1839.

Peng et al., "Reply to Dr Nielsen: Pericapsular Nerve Group (PENG) block for hip fracture," Reg Anesth Pain Med, Mar. 2019, 44(3):415-416.

Perets et al. "Intraoperative Infiltration of Liposomal Bupivacaine vs Bupivacaine Hydrochloride for Pain Management in Primary Total Hip Arthroplasty: A Prospective Randomized Trial," The Journal of Arthroplasty, 2018, 33:441-446.

Raja et al., "The revised International Association for the Study of Pain definition of pain: concepts, challenges, and compromises," PAIN, Sep. 1, 2020, 161(9):1976-1982.

Santos et al., "Is Continuous PENG Block the New 3-in-1?" J Anesth Clin Res 2019, Jun. 28, 2019, 10(6):1000898, 2 pages.

Scott et al., "Acute Toxicity of Ropivacaine Compared with that of Bupivacaine," Anesthesia and Analgesia, Nov. 1, 1989, 69(5):563-569.

Short et al., "Anatomic Study of Innervation of the Anterior Hip Capsule: Implication for Image-Guided Intervention," Regional Anesthesia and Pain Medicine, Feb. 2018, 43(2):186-192.

Surdam et al., "The Use of Exparel (Liposomal Bupivacaine) to Manage Postoperative Pain in Unilateral Total Knee Arthroplasty Patients," Journal of Arthroplasty, 2015, 30:325-329.

Therapy Services Patient Information [online] "Pubic Rami Fracture," retrieved on Jan. 11, 2023, retrieved from URL <https://www.uhd.nhs.uk/uploads/about/docs/our_publications/patient_information_leaflets/orthopaedics/Pubic_rami_fracture.pdf>, 12 pages.

(56) References Cited

OTHER PUBLICATIONS

Tran et al.., "Is pericapsular nerve group (PENG) block a true pericapsular block?," Reg Anesth Pain Med, Feb. 2019, 44(2):257.
www.sec.gov [online], "Pacira BioSciences Reports First Quarter 2019 Revenues of $91.3 Million," May 2019, retrieved on Sep. 30, 2022, retrieved from URL <https://www.sec.gov/Archives/edgar/data/1396814/000139681419000012/pcrx-3312019x991.htm>, 12 pages.
Yu et al., "Inadvertent quadriceps weakness following the pericapsular nerve group (PENG) block," Reg Anesth Pain Med, May 2019, 44(5):611-613.
Zel et al., "Neurological and Histological Outcomes After Subarachnoid Injection of a Liposomal Bupivacaine Suspension in Pigs: A Pilot Study," British Journal of Anaesthesia, Mar. 2019, 122(3):379-387.
[No Author Listed] [online], "Adductor Canal Block," RAUKvideos, uploaded on Jan. 29, 2021, retrieved on May 25, 2023, retrieved from URL <https://www.youtube.com/watch?v=DZLjNHkbMtI>, 2 pages [Video Submission].
[No Author Listed] [online], "Adductor Canal Block: What Nerves Are We After?," Regional Anesthesiology and Acute Pain Medicine, uploaded on Oct. 2, 2020, retrieved from internet on May 25, 2023, retrieved from URL <https://www.youtube.com/watch?v=fE4U7JQa2f8>, 2 pages [Video Submission].
Acharya et al., "Pericapsular Nerve Group Block: An Excellent Option for Analgesia for Positional Pain in Hip Fractures," Case Reports in Anesthesiology, Mar. 12, 2020, 2020,(1830136):1-3.
Ackmann et al., "Anatomy of the Infrapatellar Branch in Relation to Skin Incisions and as the Basis to Treat Neuropathic Pain by Percutaneous Cryodenervation," Pain Physician Journal, May/Jun. 2014, 17:E229-E348.
Bagaria et al., "The feasibility of direct adductor canal block (DACB) as a part of periarticular injection in total knee arthroplasty," Knee Surgery & Related Research, 2020, 32(48), 7 pages.
Chin et al., "Mechanisms of action of fascial plane blocks: a narrative review," Regional Anesthesia and Pain Medicine, 2021, 46:618-628.
Fiol et al., "Is There a Role for Liposomal Bupivacaine as Part of a Multimodal Strategy Inclusive of Intrathecal Morphine for Post-Cesarean Analgesia? A Retrospective Chart Review Study," Anesth. Pain Res., 2020, 4(2):1-6.
Greenky et al., "Intraoperative Surgeon Administered Adductor Canal Blockade Is Not Inferior to Anesthesiologist Administered Adductor Canal Blockade: A Prospective Randomized Trial," The Journal of Arthroplasty, 2020, 35:1228-1232.
International Preliminary Report on Patentability in International Appln. No. PCT/US2022/011828, dated Jul. 20, 2023, 16 pages.
Li et al., "Ultrasound-guided single popliteal sciatic nerve block is an effective postoperative analgesia strategy for calcaneal fracture: a randomized clinical trial," BMC Musculoskeletal Disorders, Jan. 2021, 22(735):1-9.
Matthews et al., "Surgeon-placed peripheral nerve block and continuous non-opioid analgesia in total knee arthroplasty is accessible intraoperatively: A cadaveric study," Journal of ISAKOS, Mar. 2023, 6 pages.
Matthews, "Continuous Adductor Canal & Periarticular Nerve Block for Total Knee Arthroplasty, Matthews' Placement Guide," Surgical Solutions, 2021, 6 pages.
MayfieldClinic.com [online], "Epidural Steroid Injections (ESI)," Mayfield Brain & Spine, Jul. 2018, retrieved on May 9, 2023, retrieved from URL <https://d3djccaurgtij4.cloudfront.net/pe-esi.pdf>, 3 pages.
Mont et al., "Can Joint Arthroplasty Surgeons Safely Administer Anesthesia?," The Journal of Arthroplasty, 2020, 35:1169.
Pepper et al., "Intraoperative Adductor Canal Block for Augmentation of Periarticular Injection in Total Knee Arthroplasty: A Cadaveric Study," The Journal of Arthroplasty, 2016, 31:2072-2076.
Peterson et al., "Surgeon-Performed High-Dose Bupivacaine Periarticular Injection with Intra-Articular Saphenous Nerve Block is Not Inferior to Adductor Canal Block in Total Knee Arthroplasty," The Journal of Arthroplasty, May 2020, 35:1233-1238.
Rongstad et al., "Popliteal Sciatic Nerve Block for Postoperative Analgesia," Foot & Ankle International, Jul. 1996, 17(7):378-382.
Runge et al., "The Spread of Ultrasound-Guided Injectate From the Adductor Canal to the Genicular Branch of the Posterior Obturator Nerve and the Popliteal," Regional Anesthesia and Acute Pain, Dec. 2017, 42(6):725-730.
Sveom et al., "Ultrasound-Guided Adductor Canal Block Versus Intraoperative Transarticular Saphenous Nerve Block: A Retrospective Analysis," The Journal of Arthroplasty, 2022, 37:S134-S138.
Tak et al., "Continuous adductor canal block is superior to adductor canal block alone or adductor canal block combined with IPACK block (interspace between the popliteal artery and the posterior capsule of knee) in postoperative analgesia and ambulation following continued from U): total knee arthroplasty: randomized control trial," Musculoskeletal Surg., Jun. 2022, 106:155-162.
Teachmeanatomy.info [online], "Anatomical Planes," Sep. 30, 2022, retrieved on Jun. 13, 2023, retrieved from URL <https://teachmeanatomy.info/the-basics/anatomical-terminology/planes/>, 2 pages.
Tran et al., "Evaluation of the proximal adductor canal block injectate spread: a cadaveric study," Reg. Anesth. Pain. Med., 2020, 45:124-130.
Worrell et al., "The Mayo block: an efficacious block for hallux and first metatarsal surgery," AANA Journal, Apr. 1, 1996, 64(2):146-152, Abstract only.
Yee et al., "Quadriceps Weakness After Single-Short Adductor Canal Block," The Journal of Bone and Joint Surgery, 2021, 103(1):30-36.
Domb et al., "The effect of liposomal bupivacaine injection during total hip arthroplasty: a controlled cohort study," BMC Musculoskeletal Disorders, 2014, 15(310):1-6.
Tong et al., "Liposomal bupivacaine and clinical outcomes," Best Practice & Research Clinical Anaesthesiology, 2014, 28:15-27.
[No Author Listed] [online], "Highlights of Prescribing Information—EXPAREL," accessdata.fda.gov, Apr. 2018, retrieved on Jun. 17, 2022, retrieved from URL <www.accessdata.fda.gov/drugsatfda_docs/label/2018/022496s9lbl.pdf>, 28 pages.
[No Author Listed] [online], "Marcaine [package insert]," accessdata.fda.gov, Oct. 2011, retrieved on Jun. 21, 2022, retrieved from URL <https://www.accessdata.fda.gov/drugsatfda_docs/label/2012/018692s015lbl.pdf>, 30 pages.
[No Author Listed] [online], "Naropin [package insert]," accessdata.fda.gov, Nov. 2018, retrieved on Jun. 21, 2022, retrieved from URL <https://www.accessdata.fda.gov/drugsatfda_docs/label/2018/020533s035lbl.pdf>, 30 pages.
American Society of Anesthesiologists Task Force on Acute Pain Management, "Practice guidelines for acute pain management in the perioperative setting: an updated report by the American Society of Anesthesiologists Task Force on Acute Pain Management," Anesthesiology, Feb. 2012, 116(2):248-273.
American Society of Anesthesiologists, "ASA Physical Status Classification System," asahq.org, Dec. 13, 2020, retrieved from URL <https://www.asahq.org/standards-and-guidelines/asa-physical-status-classification-system>, 4 pages.
Bigeleisen et al., "Novel approaches in pain management in cardiac surgery," Curr Opin Anaesthesiol. Feb. 2015, 28(1):89-94.
Chughtai et al., "Liposomal Bupivacaine Is Both Safe and Effective in Controlling Postoperative Pain After Spinal Surgery in Children: A Controlled Cohort Study," Clin Spine Surg., 2020, 33(10):E533-E538.
Cohen et al., "Incidence of adverse events attributable to bupivacaine liposome injectable suspension or plain bupivacaine for postoperative pain in pediatric surgical patients: A retrospective matched cohort analysis," Paediatr Anaesth., 2019, 29(2):169-174, 15 pages.
Day et al., "Extended Release Liposomal Bupivacaine Injection (Exparel) for Early Postoperative Pain Control Following Pharyngoplasty," J Craniofac Surg., Jul. 2018, 29(3):726-730, 4 pages.
Delgado et al., "Validation of Digital Visual Analog Scale Pain Scoring With a Traditional Paper-based Visual Analog Scale in Adults," J Am Acad Orthop Surg Glob Res Rev., Mar. 2018, 2(3):e088, 6 pages.

(56) References Cited

OTHER PUBLICATIONS

Ecoffey, "Refresher course: Local anesthetic pharmacology in children," Regional Anesthesia and Pain Medicine, 2015, 40(5):e23-e25.
Gan, "Poorly controlled postoperative pain: prevalence, consequences, and prevention," J Pain Res. 2017, 10:2287-2298.
Gerbershagen et al., "Pain intensity on the first day after surgery: a prospective cohort study comparing 179 surgical procedures," Anesthesiology, Apr. 2013, 118(4):934-944.
Gottschalk et al., "Quality of postoperative pain using an intraoperatively placed epidural catheter after major lumbar spinal surgery," Anesthesiology, Jul. 2004, 101(1):175-180.
Hu et al., "Pharmacokinetic profile of liposome bupivacaine injection following a single administration at the surgical site," Clin Drug Investig., 2013, 33(2):109-115.
Kim et al., "Preparation of multivesicular liposomes," Biochim. Biophys. Acta, Mar. 9, 1983, 728:(3):339-348.
Li et al., "Acute postoperative opioid consumption trajectories and long-term outcomes in pediatric patients after spine surgery," J Pain Res., 2019, 12:1673-1684.
Manna et al., "Probing the mechanism of bupivacaine drug release from multivesicular liposomes," J Control Release, Jan. 28, 2019, 294:279-287, 41 pages.
Mazoit et al., "Pharmacokinetics of bupivacaine following caudal anesthesia in infants," Anesthesiology, Mar. 1, 1988, 68(3):387-391.
Oda, "Pharmacokinetics and systemic toxicity of local anesthetics in children," Journal of anesthesia, Jun. 16, 2016, 30(4):547-550.
Patel et al., "Brachial Plexus Block with Liposomal Bupivacaine for Shoulder Surgery Improves Analgesia and Reduces Opioid Consumption: Results from a Multicenter, Randomized, Double-Blind, Controlled Trial," Pain Med., 2020, 21(2):387-400.
PCT International Search Report and Written Opinion in International Appln. No. PCT/US2022/020713, dated Jun. 14, 2022, 24 pages.
Rabbitts et al., "Presurgical psychosocial predictors of acute postsurgical pain and quality of life in children undergoing major surgery," J Pain., Mar. 2015, 16(3):226-234.
Rabbitts et al., "Trajectories of postsurgical pain in children: risk factors and impact of late pain recovery on long-term health outcomes after major surgery," Pain, Nov. 2015, 156(11):2383-2389.
Rice et al., "Pharmacokinetic Profile and Tolerability of Liposomal Bupivacaine Following a Repeated Dose via Local Subcutaneous Infiltration in Healthy Volunteers," Clin Drug Investig., 2017, 37(3):249-257.
Shah et al., "Current Trends in Pediatric Spine Deformity Surgery: Multimodal Pain Management and Rapid Recovery," Global Spine J., 2020, 10(3):346-352.
Springer et al., "Systemic Safety of Liposomal Bupivacaine in Simultaneous Bilateral Total Knee Arthroplasty," J Arthroplasty., Jan. 2018, 33(1):97-101.
Tirotta et al., "Continuous incisional infusion of local anesthetic in pediatric patients following open heart surgery," Pediatr Anaesth., Jun. 2009, 19(6):571-576.
USFaD, "Pediatric Study Plans: Content of and Process for Submitting Initial Pediatric Study Plans and Ameded Initial Pediatric Study Plans Guidance for Industry," US Food and Drug Administration, Jul. 2020, retrieved from URL <https://www.fda.gov/media/86340/download>, 26 pages.
Walker et al., "Complications in Pediatric Regional Anesthesia: An Analysis of More than 100,000 Blocks from the Pediatric Regional Anesthesia Network," Anesthesiology, Oct. 2018, 129(4):721-732.
Office Action in U.S. Appl. No. 18/239,587, dated Dec. 27, 2023, 26 pages.
U.S. Appl. No. 18/239,587, filed Aug. 29, 2023, Winston.
U.S. Appl. No. 17/719,716, filed Apr. 13, 2022, Hall et al.
U.S. Appl. No. 17/720,166, filed Apr. 13, 2022, Hall et al.
U.S. Appl. No. 17/840,104, filed Jun. 14, 2022, Hall et al.
U.S. Appl. No. 18/046,416, filed Oct. 13, 2022, Garcia et al.
U.S. Appl. No. 18/325,924, filed May 30, 2023, Hall et al.
U.S. Appl. No. 18/325,927, filed May 30, 2023, Hall et al.
International Preliminary Report on Patentability in International Application No. PCT/US2022/020713, dated Sep. 28, 2023, 18 pages.
Kanazi et al., "The Analgesic Efficacy of Subarachnoid Morphine in Comparison with Ultrasound-Guided Transversus Abdominis Plane Block After Cesarean Delivery A Randomized Controlled Trial," Anesthesia & Analgesia, Aug. 2010, 111(2):475-481.
Medilogbiohealth.com [online], "Angles of Administration of Injection—ID, IM, SC, IV," Mar. 10, 2021, retrieved on Aug. 22, 2023, retrieved from URL <https://www.medilogbiohealth.com/2021/03/injection.html>, 8 pages.
Regional Anesthesiology and Acute Pain Medicine [online], "Adductor Canal Block: What Nerves Are We After?," uploaded on Oct. 2, 2020, retrieved from URL <https://www.youtube.com/watch?v=fE4U7JQa2f>, 9 pages.
Vij et al., Liposomal Bupivacaine Decreases Post-Operative Opioid Use after Anterior Cruciate Ligament Reconstruction: A Review of Level I Evidence, Orthopedic Reviews, Aug. 5, 2022, 14(3):37159, 8 pages.

\* cited by examiner

TREATMENT OF PAIN IN PEDIATRIC PATIENTS BY ADMINISTRATION OF SUSTAINED-RELEASE LIPOSOMAL ANESTHETIC COMPOSITIONS

CROSS-REFERENCE TO RELATED APPLICATIONS

This application claims the benefit of U.S. Provisional Application No. 63/163,672, filed Mar. 19, 2021, which is incorporated by reference herein in its entirety.

BACKGROUND

Extended-release anesthetic formulations of bupivacaine have been developed to prolong the duration of analgesia. Multivesicular liposomal bupivacaine has been approved for single-dose infiltration to produce postsurgical local analgesia and as an interscalene brachial plexus nerve block to produce postsurgical regional analgesia (see EXPAREL® prescribing information, www.accessdata.fda.gov/drugsatfda_docs/label/2018/022496s91bl.pdf). It would also be desirable, however, to provide treatment for pain in pediatric patients. Children who undergo surgery often experience moderate-to-severe postsurgical pain that may be difficult to manage. When postsurgical pain is uncontrolled, patients may experience adverse outcomes, including complications, delayed healing, prolonged length of stay, and development of chronic postsurgical pain. Pain management is of particular importance for procedures such as spine and cardiac surgery because these procedures can be considerably painful during the postsurgical period.

The American Society of Anesthesiologists (ASA) recommends a multimodal approach to pain management for pediatric patients, and strategies can include nonsteroidal anti-inflammatory drugs and acetaminophen as well as local anesthesia. While the local anesthetics ropivacaine hydrochloride (HCl) and bupivacaine HCl can be used in adult patients, they are currently not approved for use in pediatric patients under the age of 12 years. Pharmacokinetic (PK) profiles of anesthetic agents may vary by age, with clearance of both ropivacaine HCl and bupivacaine HCl being lower in younger children when compared with older children and adults. Nonetheless, an observational study of data from >90,000 pediatric patients using the Pediatric Regional Anesthesia Network reported that use of local anesthetics, including ropivacaine HCl and bupivacaine HCl, was safe overall and provided comparable anesthesia to that previously observed in adults.

EXPAREL® (liposomal bupivacaine) is a long-acting formulation of bupivacaine that is approved for prolonged postsurgical analgesia in adults via local infiltration or interscalene brachial plexus nerve block. Unlike the aqueous formulation of bupivacaine HCl, in EXPAREL® the liposomal formulation of bupivacaine is encapsulated in multivesicular liposomes, allowing for the sustained release of low concentrations of bupivacaine over time. Several studies have demonstrated the safety and tolerability of liposomal bupivacaine in adults and that plasma bupivacaine levels after liposomal bupivacaine administration remain below thresholds associated with neurotoxicity and cardiotoxicity. The pharmacology of local anesthetics is generally similar between adult and pediatric patients over the age of 6 months.

There continues to be a need for a method for treating pain in a pediatric subject, such as a human child, such as a method for treating in a pediatric subjects such as a human child that does not comprise using opioids.

SUMMARY

In some embodiments provided herein is a method of treating pain in a pediatric subject, the method comprising administering to the subject a pharmaceutical composition comprising bupivacaine, wherein the composition does not comprise an opioid.

In some embodiments provided herein is a method of treating pain in a pediatric subject, the method comprising administering to the subject a pharmaceutical composition comprising bupivacaine, wherein the composition does not comprise an opioid, wherein the composition is a multivesicular liposomal particle pharmaceutical composition.

In some embodiments provided herein is a method of treating pain in a pediatric subject, the method comprising administering to the subject a pharmaceutical composition comprising bupivacaine, wherein the composition does not comprise an opioid, wherein the apparent elimination half-life of bupivacaine in the subject is from about 4 hours to about 50 hours, such as from about 4 hours to about 48 hours, such as from about 5 hours to about 45 hours, such as from about 15 hours to about 35 hours, such as from about 24.9 hours to 26.8 hours.

In some embodiments provided herein is a method of treating pain in a pediatric subject, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of treating pain in a pediatric subject, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of treating pain in a pediatric subject, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate.

In some embodiments provided herein is a method of treating pain in a pediatric subject, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of treating pain in a pediatric subject, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of treating pain in a pediatric subject, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of inducing motor block in a pediatric subject, the method comprising administering to the subject a pharmaceutical composition comprising bupivacaine, wherein the composition does not comprise an opioid.

In some embodiments provided herein is a method of inducing motor block in a pediatric subject, the method comprising administering to the subject a pharmaceutical composition comprising bupivacaine, wherein the composition does not comprise an opioid, wherein the composition is a multivesicular liposomal particle pharmaceutical composition.

In some embodiments provided herein is a method of inducing motor block in a pediatric subject, the method comprising administering to the subject a pharmaceutical composition comprising bupivacaine, wherein the composition does not comprise an opioid, wherein the apparent elimination half-life of bupivacaine in the subject is from about 4 hours to about 50 hours, such as from about 4 hours to about 48 hours, such as from about 5 hours to about 45 hours, such as from about 15 hours to about 35 hours, such as from about 24.9 hours to 26.8 hours.

In some embodiments provided herein is a method of inducing motor block in a pediatric subject, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing motor block in a pediatric subject, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing motor block in a pediatric subject, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate.

In some embodiments provided herein is a method of inducing motor block in a pediatric subject, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing motor block in a pediatric subject, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing motor block in a pediatric subject, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of inducing sensory block in a pediatric subject, the method comprising administering to the subject a pharmaceutical composition comprising bupivacaine, wherein the composition does not comprise an opioid.

In some embodiments provided herein is a method of inducing sensory block in a pediatric subject, the method comprising administering to the subject a pharmaceutical composition comprising bupivacaine, wherein the composition does not comprise an opioid, wherein the composition is a multivesicular liposomal particle pharmaceutical composition.

In some embodiments provided herein is a method of inducing sensory block in a pediatric subject, the method comprising administering to the subject a pharmaceutical composition comprising bupivacaine, wherein the composition does not comprise an opioid, wherein the apparent elimination half-life of bupivacaine in the subject is from about 4 hours to about 50 hours, such as from about 4 hours to about 48 hours, such as from about 5 hours to about 45 hours, such as from about 15 hours to about 35 hours, such as from about 24.9 hours to 26.8 hours.

In some embodiments provided herein is a method of inducing sensory block in a pediatric subject, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing sensory block in a pediatric subject, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing sensory block in a pediatric subject, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of inducing sensory block in a pediatric subject, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing sensory block in a pediatric subject, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing sensory block in a pediatric subject, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of treating pain in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of treating pain in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of treating pain in a pediatric subject that is undergoing or has undergone surgery, such as spine surgery, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of treating pain in a pediatric subject that is undergoing or has undergone surgery, such as spine surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of treating pain in a pediatric subject that is undergoing or has undergone surgery, such as spine surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of treating pain in a pediatric subject that is undergoing or has undergone surgery, such as spine surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of treating pain in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of treating pain in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of treating pain in a pediatric subject that is undergoing or has undergone surgery, such as cardiac surgery, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of treating pain in a pediatric subject that is undergoing or has undergone surgery, such as cardiac surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of treating pain in a pediatric subject that is undergoing or has undergone surgery, such as cardiac surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of treating pain in a pediatric subject that is undergoing or has undergone surgery, such as cardiac surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of inducing motor block in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing motor block in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing motor block in a pediatric subject that is undergoing or has undergone surgery, such as spine surgery, the method comprising administering to the subject a pharmaceutical composition comprising multivesicular liposomes encapsulating bupivacaine phosphate, said multivesicular liposomes comprising: bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of inducing motor block in a pediatric subject that is undergoing or has undergone surgery, such as spine surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing motor block in a pediatric subject that is undergoing or has undergone surgery, such as spine surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing motor block in a pediatric subject that is undergoing or has undergone surgery, such as spine surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
    wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of inducing motor block in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing motor block in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing motor block in a pediatric subject that is undergoing or has undergone surgery, such as cardiac surgery, the method comprising administering to the subject a pharmaceutical composition comprising multivesicular liposomes encapsulating bupivacaine phosphate, said multivesicular liposomes comprising:
    bupivacaine or a salt thereof;
    phosphoric acid;
    a lipid component comprising at least one amphipathic lipid and at least one neutral lipid lacking a hydrophilic head group; and,
    optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate.

In some embodiments provided herein is a method of inducing motor block in a pediatric subject that is undergoing or has undergone surgery, such as cardiac surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing motor block in a pediatric subject that is undergoing or has undergone surgery, such as cardiac surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing motor block in a pediatric subject that is undergoing or has undergone surgery, such as cardiac surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of inducing sensory block in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing sensory block in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing sensory block in a pediatric subject that is undergoing or has undergone surgery, such as spine surgery, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of inducing sensory block in a pediatric subject that is undergoing or has undergone surgery, such as spine surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing sensory block in a pediatric subject that is undergoing or has undergone surgery, such as spine surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing sensory block in a pediatric subject that is undergoing or has undergone surgery, such as spine surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of inducing sensory block in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing sensory block in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing sensory block in a pediatric subject that is undergoing or has undergone surgery, such as cardiac surgery, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:

a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of inducing sensory block in a pediatric subject that is undergoing or has undergone surgery, such as cardiac surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing sensory block in a pediatric subject that is undergoing or has undergone surgery, such as cardiac surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing sensory block in a pediatric subject that is undergoing or has undergone surgery, such as cardiac surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
    wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments, the method of treating pain in a pediatric subject, such as a pediatric subject that is undergoing or has undergone surgery, such as spine surgery or that is undergoing or has undergone surgery, such as cardiac surgery, comprises administering an opioid to the subject following the administration of the pharmaceutical composition to the pediatric subject. In some embodiments, the method of treating pain in a pediatric subject, such as a pediatric subject that is undergoing or has undergone surgery, such as spine surgery or such as cardiac surgery, does not comprise administering an opioid to the subject following the administration of the pharmaceutical composition to the pediatric subject.

In some embodiments, the method of treating pain in a pediatric subject, such as a pediatric subject that is undergoing or has undergone surgery, such as spine surgery or such as cardiac surgery, does not comprise administering an opioid to the subject.

In some embodiments, the method of reducing pain in a pediatric subject, such as a pediatric subject that is undergoing or has undergone surgery, such as spine surgery or such as cardiac surgery, does not comprise administering an opioid to the subject.

In some embodiments, the method of anesthetizing a pediatric subject, such as a pediatric subject that is undergoing or has undergone surgery, such as spine surgery or such as cardiac surgery, does not comprise administering an opioid to the subject.

In some embodiments, the method of inducing motor block in a pediatric subject, such as a pediatric subject that is undergoing or has undergone surgery, such as spine surgery or such as cardiac surgery, does not comprise administering an opioid to the subject.

In some embodiments, the method of inducing sensory block in a pediatric subject, such as a pediatric subject that is undergoing or has undergone surgery, such as spine surgery or such as cardiac surgery, does not comprise administering an opioid to the subject.

In some embodiments, the method of a method of reducing an amount of a non-opioid analgesic administered to a pediatric subject, such as a pediatric subject that is undergoing or has undergone surgery, such as spine surgery or such as cardiac surgery, does not comprise administering an opioid to the subject.

In some embodiments, the method of a method of reducing a duration of time during which a non-opioid analgesic is administered to a pediatric subject, such as a pediatric subject that is undergoing or has undergone surgery, such as spine surgery or such as cardiac surgery, does not comprise administering an opioid to the subject.

In some embodiments, the opioid is administered in a total amount less than 50 mg in the first about 72 hours following the administration of the pharmaceutical composition to the pediatric subject.

In some embodiments of the method of treating pain in a pediatric subject, such as a pediatric subject that is undergoing or has undergone surgery, such as spine surgery or such as cardiac surgery, wherein the pediatric subject is a first subject, in the first about 72 hours following administration of the pharmaceutical composition to the first subject the opioid is administered to the first subject in a total amount that is lower than the total amount of an opioid that is administered to a second pediatric subject in the first about 72 hours following administration to the second subject of non-liposomal bupivacaine containing the same amount of bupivacaine as the pharmaceutical composition, wherein a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, is not administered to the second subject.

In some embodiments of the method of treating pain in a pediatric subject, such as a pediatric subject that is undergoing or has undergone surgery, such as spine surgery or such as cardiac surgery, wherein the pediatric subject is a first subject, in the first about 72 hours following administration of the pharmaceutical composition to the first subject the opioid is administered to the first subject in a total amount that is lower than the total amount of an opioid that is administered to a second pediatric subject in the first about 72 hours following administration to the second subject of non-liposomal bupivacaine containing the same amount of bupivacaine as the pharmaceutical composition, wherein a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome, is not administered to the second subject.

In some embodiments of the method of treating pain in a pediatric subject, such as a pediatric subject that is undergoing or has undergone surgery, such as spine surgery or such as cardiac surgery, wherein the pediatric subject is a first subject, in the first about 72 hours following administration of the pharmaceutical composition to the first subject the opioid is administered to the first subject in a total amount that is lower than the total amount of an opioid that is administered to a second pediatric subject in the first about 72 hours following administration to the second subject of non-liposomal bupivacaine containing the same amount of bupivacaine as the pharmaceutical composition, wherein a pharmaceutical composition comprising multivesicular liposomes encapsulating bupivacaine phosphate, said multivesicular liposomes comprising:

bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
is not administered to the second subject.

In some embodiments of the method of treating pain in a pediatric subject, such as a pediatric subject that is undergoing or has undergone surgery, such as spine surgery or such as cardiac surgery, wherein the pediatric subject is a first subject, in the first about 72 hours following administration of the pharmaceutical composition to the first subject the opioid is administered to the first subject in a total amount that is lower than the total amount of an opioid that is administered to a second pediatric subject in the first about 72 hours following administration to the second subject of non-liposomal bupivacaine containing the same amount of bupivacaine as the pharmaceutical composition, wherein a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, is not administered to the second subject.

In some embodiments of the method of treating pain in a pediatric subject, such as a pediatric subject that is undergoing or has undergone surgery, such as spine surgery or such as cardiac surgery, wherein the pediatric subject is a first subject, in the first about 72 hours following administration of the pharmaceutical composition to the first subject the opioid is administered to the first subject in a total amount that is lower than the total amount of an opioid that is administered to a second pediatric subject in the first about 72 hours following administration to the second subject of non-liposomal bupivacaine containing the same amount of bupivacaine as the pharmaceutical composition, wherein a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, is not administered to the second subject.

In some embodiments of the method of treating pain in a pediatric subject, such as a pediatric subject that is undergoing or has undergone surgery, such as spine surgery or such as cardiac surgery, wherein the pediatric subject is a first subject, in the first about 72 hours following administration of the pharmaceutical composition to the first subject the opioid is administered to the first subject in a total amount that is lower than the total amount of an opioid that is administered to a second pediatric subject in the first about 72 hours following administration to the second subject of non-liposomal bupivacaine containing the same amount of bupivacaine as the pharmaceutical composition, wherein a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, is not administered to the second subject.

In some embodiments, each of the first subject and the second subject is undergoing or has undergone spine surgery. In some embodiments, each of the first subject and the second subject is undergoing or has undergone cardiac surgery.

DETAILED DESCRIPTION

Figure 1:
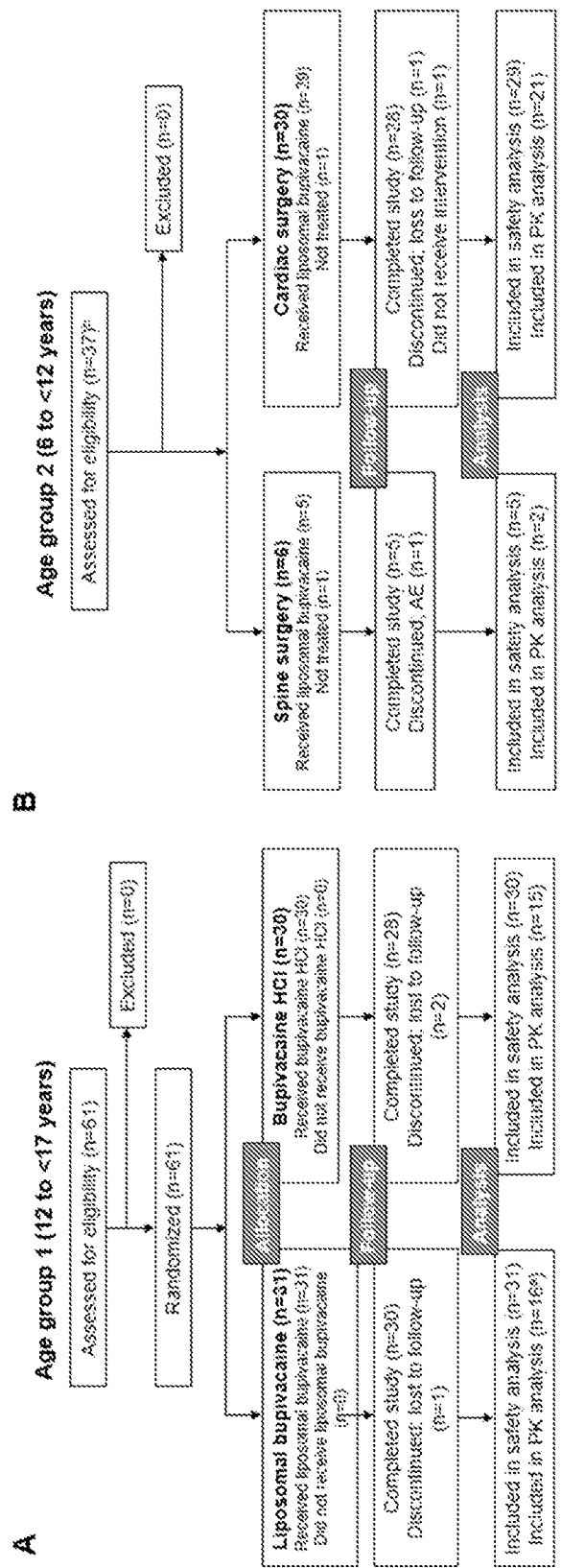
FIG. 1 shows the patient disposition for age group 1 (A) and age group 2 (B). [a]1 patient was excluded from all PK calculations because no blood samples were obtained from this patient after 1.25 hours. [b]One patient was not treated and the surgery type was not available. AE, adverse event; HCl, hydrochloride; PK, pharmacokinetics.

In some embodiments provided herein is a method of treating pain in a pediatric subject, the method comprising administering to the subject a pharmaceutical composition comprising bupivacaine, wherein the composition does not comprise an opioid.

In some embodiments provided herein is a method of treating pain in a pediatric subject, the method comprising administering to the subject a pharmaceutical composition comprising bupivacaine, wherein the composition does not comprise an opioid, wherein the composition is a multivesicular liposomal particle pharmaceutical composition.

In some embodiments provided herein is a method of treating pain in a pediatric subject, the method comprising administering to the subject a pharmaceutical composition comprising bupivacaine, wherein the composition does not comprise an opioid, wherein the apparent elimination half-life of bupivacaine in the subject is from about 4 hours to about 50 hours, such as from about 4 hours to about 48 hours, such as from about 5 hours to about 45 hours, such as from about 15 hours to about 35 hours, such as from about 24.9 hours to 26.8 hours.

In some more particular embodiments of the methods of treating pain in a pediatric subject, the pediatric subject is a subject that is undergoing or has undergone spine surgery. In some more particular embodiments, the pediatric subject is a subject that is undergoing or has undergone cardiac surgery.

In some embodiments provided herein is a method of treating pain in a pediatric subject, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of treating pain in a pediatric subject, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of treating pain in a pediatric subject, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate.

In some embodiments provided herein is a method of treating pain in a pediatric subject, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of treating pain in a pediatric subject, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of treating pain in a pediatric subject, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of treating pain in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of treating pain in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of treating pain in a pediatric subject that is undergoing or has undergone surgery, such as spine surgery, the method comprising administering to the subject a pharmaceutical composition comprising multivesicular liposomes encapsulating bupivacaine phosphate, said multivesicular liposomes comprising:

bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of treating pain in a pediatric subject that is undergoing or has undergone surgery, such as spine surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of treating pain in a pediatric subject that is undergoing or has undergone surgery, such as spine surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of treating pain in a pediatric subject that is undergoing or has undergone surgery, such as spine surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of treating pain in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of treating pain in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of treating pain in a pediatric subject that is undergoing or has undergone surgery, such as cardiac surgery, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of treating pain in a pediatric subject that is undergoing or has undergone surgery, such as cardiac surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of treating pain in a pediatric subject that is undergoing or has undergone surgery, such as cardiac surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of treating pain in a pediatric subject that is undergoing or has undergone surgery, such as cardiac surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of anesthetizing a pediatric subject, the method comprising administering to the subject a pharmaceutical composition comprising bupivacaine, wherein the composition does not comprise an opioid.

In some embodiments provided herein is a method of anesthetizing a pediatric subject, the method comprising administering to the subject a pharmaceutical composition comprising bupivacaine, wherein the composition does not comprise an opioid, wherein the composition is a multivesicular liposomal particle pharmaceutical composition.

In some embodiments provided herein is a method of anesthetizing a pediatric subject, the method comprising administering to the subject a pharmaceutical composition comprising bupivacaine, wherein the composition does not comprise an opioid, wherein the apparent elimination half-life of bupivacaine in the subject is from about 4 hours to about 50 hours, such as from about 4 hours to about 48 hours, such as from about 5 hours to about 45 hours, such as from about 15 hours to about 35 hours, such as from about 24.9 hours to 26.8 hours.

In some more particular embodiments of the methods of anesthetizing a pediatric subject, the pediatric subject is a subject that is undergoing or has undergone spine surgery. In some more particular embodiments, the pediatric subject is a subject that is undergoing or has undergone cardiac surgery.

In some embodiments provided herein is a method of anesthetizing a pediatric subject in need thereof, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of anesthetizing a pediatric subject in need thereof, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of anesthetizing a pediatric subject in need thereof, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of anesthetizing a pediatric subject in need thereof, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of anesthetizing a pediatric subject in need thereof, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of anesthetizing a pediatric subject in need thereof, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of anesthetizing a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of anesthetizing a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of anesthetizing a pediatric subject that is undergoing or has undergone surgery, such as spine surgery, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of anesthetizing a pediatric subject that is undergoing or has undergone surgery, such as spine surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of anesthetizing a pediatric subject that is undergoing or has undergone surgery, such as spine surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of anesthetizing a pediatric subject that is undergoing or has undergone surgery, such as spine surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of anesthetizing a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of anesthetizing a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of anesthetizing a pediatric subject that is undergoing or has undergone surgery, such as cardiac surgery, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of anesthetizing a pediatric subject that is undergoing or has undergone surgery, such as cardiac surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of anesthetizing a pediatric subject that is undergoing or has undergone surgery, such as cardiac surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of anesthetizing a pediatric subject that is undergoing or has undergone surgery, such as cardiac surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing pain in pediatric subject, the method comprising administering to the subject a pharmaceutical composition comprising bupivacaine, wherein the composition does not comprise an opioid.

In some embodiments provided herein is a method of reducing pain in a pediatric subject, the method comprising administering to the subject a pharmaceutical composition comprising bupivacaine, wherein the composition does not comprise an opioid, wherein the composition is a multivesicular liposomal particle pharmaceutical composition.

In some embodiments provided herein is a method of reducing pain in a pediatric subject, the method comprising administering to the subject a pharmaceutical composition comprising bupivacaine, wherein the composition does not comprise an opioid, wherein the apparent elimination half-life of bupivacaine in the subject is from about 4 hours to about 50 hours, such as from about 4 hours to about 48 hours, such as from about 5 hours to about 45 hours, such as from about 15 hours to about 35 hours, such as from about 24.9 hours to 26.8 hours.

In some more particular embodiments of the methods of reducing pain in a pediatric subject, the pediatric subject is a subject that is undergoing or has undergone spine surgery. In some more particular embodiments, the pediatric subject is a subject that is undergoing or has undergone cardiac surgery.

In some embodiments provided herein is a method of reducing pain in a pediatric subject, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing pain in a pediatric subject, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing pain in a pediatric subject, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of reducing pain in a pediatric subject, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing pain in a pediatric subject, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing pain in a pediatric subject, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing pain in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing pain in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing pain in a pediatric subject that is undergoing or has undergone surgery, such as spine surgery, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of reducing pain in a pediatric subject that is undergoing or has undergone surgery, such as spine surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing pain in a pediatric subject that is undergoing or has undergone surgery, such as spine surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing pain in a pediatric subject that is undergoing or has undergone surgery, such as spine surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing pain in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing pain in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing pain in a pediatric subject that is undergoing or has undergone surgery, such as cardiac surgery, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of reducing pain in a pediatric subject that is undergoing or has undergone surgery, such as cardiac surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing pain in a pediatric subject that is undergoing or has undergone surgery, such as cardiac surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing pain in a pediatric subject that is undergoing or has undergone surgery, such as cardiac surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing an amount of an analgesic, such as an opioid, administered to a pediatric subject in need thereof, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing an amount of an analgesic, such as an opioid, administered to a pediatric subject in need thereof, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing an amount of an analgesic, such as an opioid, administered to a pediatric subject in need thereof, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:

a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of reducing an amount of an analgesic, such as an opioid, administered to a pediatric subject in need thereof, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing an amount of an analgesic, such as an opioid, administered to a pediatric subject in need thereof, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing an amount of an analgesic, such as an opioid, administered to a pediatric subject in need thereof, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing an amount of an analgesic, such as an opioid, administered to a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing an amount of an analgesic, such as an opioid, administered to a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing an amount of an analgesic, such as an opioid, administered to a pediatric subject that is undergoing or has undergone surgery, such as spine surgery, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of reducing an amount of an analgesic, such as an opioid, administered to a pediatric subject that is undergoing or has undergone surgery, such as spine surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing an amount of an analgesic, such as an opioid, administered to a pediatric subject that is undergoing or has undergone surgery, such as spine surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing an amount of an analgesic, such as an opioid, administered to a pediatric subject that is undergoing or has undergone surgery, such as spine surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing an amount of an analgesic, such as an opioid, administered to a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing an amount of an analgesic, such as an opioid, administered to a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing an amount of an analgesic, such as an opioid, administered to a pediatric subject that is undergoing or has undergone surgery, such as cardiac surgery, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of reducing an amount of an analgesic, such as an opioid, administered to a pediatric subject that is undergoing or has undergone surgery, such as cardiac surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing an amount of an analgesic, such as an opioid, administered to a pediatric subject that is undergoing or has undergone surgery, such as cardiac surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing an amount of an analgesic, such as an opioid, administered to a pediatric subject that is undergoing or has undergone surgery, such as cardiac surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some more particular embodiments of the methods where the analgesic, such as an opioid, is administered to the pediatric subject, the analgesic is administered following a surgical procedure in the subject. In some embodiments the analgesic reduces pain in the subject following the surgical procedure.

In some embodiments provided herein is a method of reducing a duration of time during which an analgesic, such as an opioid, is administered to a pediatric subject in need thereof, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing a duration of time during which an analgesic, such as an opioid, is administered to a pediatric subject in need thereof, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing a duration of time during which an analgesic, such as an opioid, is administered to a pediatric subject in need thereof, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of reducing a duration of time during which an analgesic, such as an opioid, is administered to a pediatric subject in need thereof, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing a duration of time during which an analgesic, such as an opioid, is administered to a pediatric subject in need thereof, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing a duration of time during which an analgesic, such as an opioid, is administered to a pediatric subject in need thereof, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing a duration of time during which an analgesic, such as an opioid, is administered to a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing a duration of time during which an analgesic, such as an opioid, is administered to a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing a duration of time during which an analgesic, such as an opioid, is administered to a pediatric subject that is undergoing or has undergone surgery, such as spine surgery, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of reducing a duration of time during which an analgesic, such as an opioid, is administered to a pediatric subject that is undergoing or has undergone surgery, such as spine surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing a duration of time during which an analgesic, such as an opioid, is administered to a pediatric subject that is undergoing or has undergone surgery, such as spine surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing a duration of time during which an analgesic, such as an opioid, is administered to a pediatric subject that is undergoing or has undergone surgery, such as spine surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing a duration of time during which an analgesic, such as an opioid, is administered to a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing a duration of time during which an analgesic, such as an opioid, is administered to a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing a duration of time during which an analgesic, such as an opioid, is administered to a pediatric subject that is undergoing or has undergone surgery, such as cardiac surgery, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;

c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate.

In some embodiments provided herein is a method of reducing a duration of time during which an analgesic, such as an opioid, is administered to a pediatric subject that is undergoing or has undergone surgery, such as cardiac surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing a duration of time during which an analgesic, such as an opioid, is administered to a pediatric subject that is undergoing or has undergone surgery, such as cardiac surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing a duration of time during which an analgesic, such as an opioid, is administered to a pediatric subject that is undergoing or has undergone surgery, such as cardiac surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some more particular embodiments of the methods where the analgesic, such as an opioid, is administered to the pediatric subject, the analgesic is administered following a surgical procedure in the subject. In some embodiments the analgesic reduces pain in the subject following the surgical procedure.

In some embodiments provided herein is a method of reducing an amount of a non-opioid analgesic administered to a pediatric subject, the method comprising administering to the subject a pharmaceutical composition comprising bupivacaine, wherein the composition does not comprise an opioid.

In some embodiments provided herein is a method of reducing an amount of a non-opioid analgesic administered to a pediatric subject, the method comprising administering to the subject a pharmaceutical composition comprising bupivacaine, wherein the composition does not comprise an opioid, wherein the composition is a multivesicular liposomal particle pharmaceutical composition.

In some embodiments provided herein is a method of reducing an amount of a non-opioid analgesic administered to a pediatric subject, the method comprising administering to the subject a pharmaceutical composition comprising bupivacaine, wherein the composition does not comprise an opioid, wherein the apparent elimination half-life of bupivacaine in the subject is from about 4 hours to about 50 hours, such as from about 4 hours to about 48 hours, such as from about 5 hours to about 45 hours, such as from about 15 hours to about 35 hours, such as from about 24.9 hours to 26.8 hours.

In some more particular embodiments of the methods of reducing an amount of a non-opioid analgesic administered to a pediatric subject, the pediatric subject is a subject that is undergoing or has undergone spine surgery. In some more particular embodiments, the pediatric subject is a subject that is undergoing or has undergone cardiac surgery.

In some embodiments provided herein is a method of reducing an amount of a non-opioid analgesic administered to a pediatric subject in need thereof, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing an amount of a non-opioid analgesic administered to a pediatric subject in need thereof, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing an amount of a non-opioid analgesic administered to a pediatric subject in need thereof, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of reducing an amount of a non-opioid analgesic administered to a pediatric subject in need thereof, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing an amount of a non-opioid analgesic administered to a pediatric subject in need thereof, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing an amount of a non-opioid analgesic administered to a pediatric subject in need thereof, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some more particular embodiments of the methods where the non-opioid analgesic is administered to the pediatric subject, the non-opioid analgesic is administered following a surgical procedure in the subject. In some embodiments the non-opioid analgesic reduces pain in the subject following the surgical procedure.

In some embodiments provided herein is a method of reducing an amount of a non-opioid analgesic administered to a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing an amount of a non-opioid analgesic administered to a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing an amount of a non-opioid analgesic administered to a pediatric subject that is undergoing or has undergone surgery, such as spine surgery, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate.

In some embodiments provided herein is a method of reducing an amount of a non-opioid analgesic administered to a pediatric subject that is undergoing or has undergone surgery, such as spine surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing an amount of a non-opioid analgesic administered to a pediatric subject that is undergoing or has undergone surgery, such as spine surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing an amount of a non-opioid analgesic administered to a pediatric subject that is undergoing or has undergone surgery, such as spine surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing an amount of a non-opioid analgesic administered to a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing an amount of a non-opioid analgesic administered to a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing an amount of a non-opioid analgesic administered to a pediatric subject that is undergoing or has undergone surgery, such as cardiac surgery, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:

a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of reducing an amount of a non-opioid analgesic administered to a pediatric subject that is undergoing or has undergone surgery, such as cardiac surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing an amount of a non-opioid analgesic administered to a pediatric subject that is undergoing or has undergone surgery, such as cardiac surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing an amount of a non-opioid analgesic administered to a pediatric subject that is undergoing or has undergone surgery, such as cardiac surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
    wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing a duration of time during which a non-opioid analgesic is administered to a pediatric subject, the method comprising administering to the subject a pharmaceutical composition comprising bupivacaine, wherein the composition does not comprise an opioid.

In some embodiments provided herein is a method of reducing a duration of time during which a non-opioid analgesic is administered to a pediatric subject, the method comprising administering to the subject a pharmaceutical composition comprising bupivacaine, wherein the composition does not comprise an opioid, wherein the composition is a multivesicular liposomal particle pharmaceutical composition.

In some embodiments provided herein is a method of reducing a duration of time during which a non-opioid analgesic is administered to a pediatric subject, the method comprising administering to the subject a pharmaceutical composition comprising bupivacaine, wherein the composition does not comprise an opioid, wherein the apparent elimination half-life of bupivacaine in the subject is from about 4 hours to about 50 hours, such as from about 4 hours to about 48 hours, such as from about 5 hours to about 45 hours, such as from about 15 hours to about 35 hours, such as from about 24.9 hours to 26.8 hours.

In some more particular embodiments of the methods of reducing a duration of time during which a non-opioid analgesic is administered to a pediatric subject, the pediatric subject is a subject that is undergoing or has undergone spine surgery. In some more particular embodiments, the pediatric subject is a subject that is undergoing or has undergone cardiac surgery.

In some embodiments provided herein is a method of reducing a duration of time during which a non-opioid analgesic is administered to a pediatric subject in need thereof, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing a duration of time during which a non-opioid analgesic is administered to a pediatric subject in need thereof, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing a duration of time during which a non-opioid analgesic is administered to a pediatric subject in need thereof, the method comprising administering to the subject a pharmaceutical composition comprising multivesicular liposomes encapsulating bupivacaine phosphate, said multivesicular liposomes comprising:
    bupivacaine or a salt thereof;
    phosphoric acid;
    a lipid component comprising at least one amphipathic lipid and at least one neutral lipid lacking a hydrophilic head group; and,
    optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate.

In some embodiments provided herein is a method of reducing a duration of time during which a non-opioid analgesic is administered to a pediatric subject in need thereof, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing a duration of time during which a non-opioid analgesic is administered to a pediatric subject in need thereof, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing a duration of time during which a non-opioid analgesic is administered to a pediatric subject in need thereof, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some more particular embodiments of the methods where the non-opioid analgesic is administered to the subject, the non-opioid analgesic is administered following a surgical procedure in the subject. In some embodiments the non-opioid analgesic reduces pain in the subject following the surgical procedure.

In some embodiments provided herein is a method of reducing a duration of time during which a non-opioid analgesic is administered to a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing a duration of time during which a non-opioid analgesic is administered to a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing a duration of time during which a non-opioid analgesic is administered to a pediatric subject that is undergoing or has undergone surgery, such as spine surgery, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and e) removing the organic solvent from the solvent spherules to form multivesicular liposomes encapsulating bupivacaine phosphate.

In some embodiments provided herein is a method of reducing a duration of time during which a non-opioid analgesic is administered to a pediatric subject that is undergoing or has undergone surgery, such as spine surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing a duration of time during which a non-opioid analgesic is administered to a pediatric subject that is undergoing or has undergone surgery, such as spine surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing a duration of time during which a non-opioid analgesic is administered to a pediatric subject that is undergoing or has undergone surgery, such as spine surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing a duration of time during which a non-opioid analgesic is administered to a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing a duration of time during which a non-opioid analgesic is administered to a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing a duration of time during which a non-opioid analgesic is administered to a pediatric subject that is undergoing or has undergone surgery, such as cardiac surgery, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and, optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of reducing a duration of time during which a non-opioid analgesic is administered to a pediatric subject that is undergoing or has undergone surgery, such as cardiac surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing a duration of time during which a non-opioid analgesic is administered to a pediatric subject that is undergoing or has undergone surgery, such as cardiac surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing a duration of time during which a non-opioid analgesic is administered to a pediatric subject that is undergoing or has undergone surgery, such as cardiac surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of inducing motor block in a pediatric subject, the method comprising administering to the subject a pharmaceutical composition comprising bupivacaine, wherein the composition does not comprise an opioid.

In some embodiments provided herein is a method of inducing motor block in a pediatric subject, the method comprising administering to the subject a pharmaceutical composition comprising bupivacaine, wherein the composition does not comprise an opioid, wherein the composition is a multivesicular liposomal particle pharmaceutical composition.

In some embodiments provided herein is a method of inducing motor block in a pediatric subject, the method comprising administering to the subject a pharmaceutical composition comprising bupivacaine, wherein the composition does not comprise an opioid, wherein the apparent elimination half-life of bupivacaine in the subject is from about 4 hours to about 50 hours, such as from about 4 hours to about 48 hours, such as from about 5 hours to about 45 hours, such as from about 15 hours to about 35 hours, such as from about 24.9 hours to 26.8 hours.

In some more particular embodiments of the methods of inducing motor block in a pediatric subject, the pediatric subject is a subject that is undergoing or has undergone spine surgery. In some more particular embodiments, the pediatric subject is a subject that is undergoing or has undergone cardiac surgery.

In some embodiments provided herein is a method of inducing motor block in a pediatric subject, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing motor block in a pediatric subject, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing motor block in a pediatric subject, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of inducing motor block in a pediatric subject, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing motor block in a pediatric subject, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing motor block in a pediatric subject, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments, the motor block has a shorter duration than the motor block induced by administering to the subject non-liposomal bupivacaine containing the same amount of bupivacaine as the pharmaceutical composition disclosed herein. In some embodiments, administering to the subject a pharmaceutical composition as disclosed herein induces a motor block having a duration of about 12 hours or less, or from about 12 hours to about 24 hours, or from about 24 hours to about 48 hours, or from about 48 hours to about 72 hours.

In some embodiments provided herein is a method of inducing sensory block in a pediatric subject, the method comprising administering to the subject a pharmaceutical composition comprising bupivacaine, wherein the composition does not comprise an opioid.

In some embodiments provided herein is a method of inducing sensory block in a pediatric subject, the method comprising administering to the subject a pharmaceutical composition comprising bupivacaine, wherein the composition does not comprise an opioid, wherein the composition is a multivesicular liposomal particle pharmaceutical composition.

In some embodiments provided herein is a method of inducing sensory block in a pediatric subject, the method comprising administering to the subject a pharmaceutical composition comprising bupivacaine, wherein the composition does not comprise an opioid, wherein the apparent elimination half-life of bupivacaine in the subject is from about 4 hours to about 50 hours, such as from about 4 hours to about 48 hours, such as from about 5 hours to about 45 hours, such as from about 15 hours to about 35 hours, such as from about 24.9 hours to 26.8 hours.

In some more particular embodiments of the methods of inducing sensory block in a pediatric subject, the pediatric subject is a subject that is undergoing or has undergone spine surgery. In some more particular embodiments, the pediatric subject is a subject that is undergoing or has undergone cardiac surgery.

In some embodiments provided herein is a method of inducing sensory block in a pediatric subject, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing sensory block in a pediatric subject, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing sensory block in a pediatric subject, the method comprising administering to the subject a pharmaceutical composition comprising multivesicular liposomes encapsulating bupivacaine phosphate, said multivesicular liposomes comprising:

bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of inducing sensory block in a pediatric subject, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing sensory block in a pediatric subject, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing sensory block in a pediatric subject, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of inducing motor block in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing motor block in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing motor block in a pediatric subject that is undergoing or has undergone surgery, such as spine surgery, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of inducing motor block in a pediatric subject that is undergoing or has undergone surgery, such as spine surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing motor block in a pediatric subject that is undergoing or has undergone surgery, such as spine surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing motor block in a pediatric subject that is undergoing or has undergone surgery, such as spine surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of inducing motor block in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing motor block in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing motor block in a pediatric subject that is undergoing or has undergone surgery, such as cardiac surgery, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of inducing motor block in a pediatric subject that is undergoing or has undergone surgery, such as cardiac surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing motor block in a pediatric subject that is undergoing or has undergone surgery, such as cardiac surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing motor block in a pediatric subject that is undergoing or has undergone surgery, such as cardiac surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of inducing sensory block in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing sensory block in a pediatric subject that is undergoing or has undergone surgery, such as spine surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing sensory block in a pediatric subject that is undergoing or has undergone surgery, such as spine surgery, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of inducing sensory block in a pediatric subject that is undergoing or has undergone surgery, such as spine surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing sensory block in a pediatric subject that is undergoing or has undergone surgery, such as spine surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing sensory block in a pediatric subject that is undergoing or has undergone surgery, such as spine surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of inducing sensory block in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing sensory block in a pediatric subject that is undergoing or has undergone surgery, such as cardiac surgery, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing sensory block in a pediatric subject that is undergoing or has undergone surgery, such as cardiac surgery, the method comprising administering to the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of inducing sensory block in a pediatric subject that is undergoing or has undergone surgery, such as cardiac surgery, the method comprising administering to the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing sensory block in a pediatric subject that is undergoing or has undergone surgery, such as cardiac surgery, the method comprising administering to the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing sensory block in a pediatric subject that is undergoing or has undergone surgery, such as cardiac surgery, the method comprising administering to the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments, the sensory block has a longer duration than the motor block induced by administering to the subject the same amount of the pharmaceutical composition.

In some embodiments, the sensory block has a longer duration than the sensory block induced by administering to the subject non-liposomal bupivacaine containing the same amount of bupivacaine as the pharmaceutical composition disclosed herein. In some embodiments, administering to the subject a pharmaceutical composition as disclosed herein induces a sensory block having a duration of from about 24 hours to about 72 hours, such as from about 24 hours to about 48 hours, such as from about 48 hours to about 72 hours. In some embodiments, administering to the subject a pharmaceutical composition described herein reduces pain for a longer period of time than the duration of the motor block induced by administering to the subject the same amount of the pharmaceutical composition. Accordingly, in some embodiments of the method comprising administering to the subject a pharmaceutical composition described herein, wherein an analgesic, such as an opioid, or such as a non-opioid analgesic, is administered to the subject, the analgesic is administered after offset of the motor block.

In some embodiments of the methods provided herein of treating pain in a pediatric subject, such as a pediatric subject that is undergoing or has undergone surgery, such as spine surgery or cardiac surgery, the method does not comprise administering an opioid to the subject.

In some embodiments of the methods provided herein of inducing motor block in a pediatric subject, such as a pediatric subject that is undergoing or has undergone surgery, such as spine surgery or cardiac surgery, the method does not comprise administering an opioid to the subject.

In some embodiments of the methods provided herein of inducing sensory block in a pediatric subject, such as a pediatric subject that is undergoing or has undergone surgery, such as spine surgery or cardiac surgery, the method does not comprise administering an opioid to the subject.

In some embodiments of the methods provided herein of reducing pain in a pediatric subject, such as a pediatric subject that is undergoing or has undergone surgery, such as spine surgery or cardiac surgery, the method does not comprise administering an opioid to the subject.

In some embodiments of the methods provided herein of reducing an amount of an analgesic administered to a pediatric subject, such as a pediatric subject that is undergoing or has undergone surgery, such as spine surgery or cardiac surgery, the method does not comprise administering an opioid to the subject.

In some embodiments of the methods provided herein of reducing a duration of time during which an analgesic is administered to a pediatric subject, such as a pediatric subject that is undergoing or has undergone surgery, such as spine surgery or cardiac surgery, the method does not comprise administering an opioid to the subject.

In some embodiments the at least one polyhydroxy carboxylic acid is selected from the group consisting of glucuronic acid, gluconic acid and tartaric acid.

In some embodiments the amphipathic lipid is selected from the group consisting of phosphatidylcholines, phosphatidylethanolamines, sphingomyelins, lysophosphatidylcholines, lysophosphatidylethanolamines, phosphatidylglycerol s, phosphatidyl serines, phosphatidylinositols, phosphatidic acids, cardiolipins, diacyl dimethylammonium propanes, and stearylamines.

In some embodiments the neutral lipid comprises at least one triglyceride.

In some embodiments the method comprises administering a therapeutically effective amount of the pharmaceutical composition.

In some embodiments the pharmaceutical composition comprises a therapeutically effective amount of bupivacaine phosphate. In some embodiments the amount of the pharmaceutical composition described herein is equivalent to from about 100 mg to about 300 mg of bupivacaine. In some embodiments the amount of the pharmaceutical composition described herein is equivalent to from about 133 mg to about 266 mg of bupivacaine. In some embodiments the amount of the pharmaceutical composition described herein is equivalent to from about 10 mg to about 70 mg of bupivacaine, such as from about 13.3 mg to about 66.5 mg of bupivacaine. In some embodiments the amount of the pharmaceutical composition described herein is equivalent to from about 10 mg to about 60 mg of bupivacaine. In some embodiments the amount of the pharmaceutical composition described herein is equivalent to from about 20 mg to about 60 mg of bupivacaine. In some embodiments the amount of the pharmaceutical composition described herein is equivalent to from about 20 mg to about 50 mg of bupivacaine. In some embodiments the amount of the pharmaceutical composition described herein is equivalent to from about 20 mg to about 40 mg of bupivacaine. In some embodiments the amount of the pharmaceutical composition described herein is equivalent to from about 20 mg to about 30 mg of bupivacaine. In some embodiments the amount of the pharmaceutical composition described herein is equivalent to from about 30 mg to about 60 mg of bupivacaine. In some embodiments the amount of the pharmaceutical composition described herein is equivalent to from about 30 mg to about 50 mg of bupivacaine. In some embodiments the amount of the pharmaceutical composition described herein is equivalent to from about 30 mg to about 40 mg of bupivacaine.

In some embodiments the amount of the pharmaceutical composition described herein is equivalent to from about 3 mg/kg to 5 mg/kg of bupivacaine, such as about 4 mg/kg of bupivacaine, where "/kg" refers to the weight of the pediatric patient, provided that the amount of the pharmaceutical composition does not exceed an amount equivalent to 266 mg of bupivacaine.

In some embodiments, the pain that may be treated according to the methods disclosed herein is in a region below the diaphragm. In some embodiments, the pain is selected from abdomen pain, lower back pain, hip pain, pelvic pain, femur pain, knee pain, foot pain, and ankle pain.

In some embodiments, the pain is abdomen pain.
In some embodiments, the pain is lower back pain.
In some embodiments, the pain is hip pain.
In some embodiments, the pain is pelvic pain.
In some embodiments, the pain is femur pain.
In some embodiments, the pain is knee pain.
In some embodiments, the pain is foot pain.
In some embodiments, the pain is ankle pain.

In some embodiments, the pain is spine pain. In some embodiments, the pain is spine pain following spine surgery.

In some embodiments, the pain is cardiac pain. In some embodiments, the pain is cardiac pain following cardiac surgery.

In some embodiments of the methods herein, the pediatric subject is undergoing spine surgery.

In some embodiments of the methods herein, the pediatric subject has undergone spine surgery.

In some embodiments of the methods herein, the pediatric subject is undergoing cardiac surgery.

In some embodiments of the methods herein, the pediatric subject has undergone cardiac surgery.

In some embodiments of the methods herein, the pediatric subject is a subject in need of the treatment or treatments disclosed herein.

In some embodiments of the methods herein, the pediatric subject is a human whose age is from 6 years old to less than 12 years old.

In some embodiments of the methods herein, the pediatric subject is a human whose age is from 12 years old to less than 17 years old.

In some embodiments of the methods herein, the pediatric subject is a non-human mammal.

In some embodiments the method comprises administering the pharmaceutical composition by epidural injection.

In some embodiments the method does not comprise administering the pharmaceutical composition by epidural injection.

In some embodiments the method comprises administering an analgesic, such as an opioid, to the pediatric subject following administration of the pharmaceutical composition to the subject.

In some embodiments of the methods herein, the opioid is administered in a total amount less than 200 mg, such as less than 100 mg, such as less than 50 mg, such as less than 25 mg, such as less than 15 mg, in the first about 72 hours following the administration of the pharmaceutical composition to the subject. In some embodiments, the opioid is oxycodone and the method comprises administering oxycodone in a total amount less than 15 mg.in the first about 72 hours following the administration of the pharmaceutical composition to the subject. In some embodiments, the method comprises administering one or more morphinans to the subject. In some embodiments, the method comprises administering morphine to the subject. In some more particular embodiments, the morphine is administered to the subject for up to 72 hours following the administration of the pharmaceutical composition to the subject.

In some embodiments, the method comprises administering one or more analgesics to the subject, such as one or more non-opioid analgesics, such as one or more NSAIDs to the subject, following, prior to or together with the administration of the pharmaceutical composition to the subject. Examples of such analgesics include NSAIDs. Examples of analgesics that may be administered following, prior to or together with the administration of the pharmaceutical composition include meloxicam, ibuprofen, naproxen, diclofenac, celecoxib, mefenamic acid, etoricoxib, indomethacin, aspirin, acetaminophen, and gabapentin. In some embodiments, the one or more non-opioid analgesics are combined with the bupivacaine in the pharmaceutical composition.

In some embodiments, the method comprises administering one or more of ketorolac, acetaminophen or ibuprofen to the subject. In some embodiments, the method comprises administering two or more of ketorolac, acetaminophen or ibuprofen to the subject. In some embodiments, the method comprises administering ketorolac, acetaminophen and ibuprofen to the subject. In some more particular embodiments, the analgesic, such as the NSAID, such as the one or more of ketorolac, acetaminophen or ibuprofen, is administered to the subject for up to 72 hours following the administration of the pharmaceutical composition to the subject.

In some embodiments, the subject has an AUC for VAS pain intensity scores over the first 72 hours following the administration of the pharmaceutical composition to the subject of from about 100 to about 200, such as about 125 to 175, such as about 140 to 160, such as about 150, such as about 147.9.

In some embodiments of the methods herein, the subject has a pruritus score as determined by the 5-D itch scale of about 10 to 20, such as about 12 to 18, such as about 13 to 16, such as about 14 to 15.

In some embodiments of the methods herein, the plasma $C_{max}$ of bupivacaine in the subject is about 150 ng/mL to about 250 ng/mL, such as about 175 ng/mL to about 225 ng/mL, such as about 200 ng/mL, such as about 210 mg/mL, for an amount of the pharmaceutical composition described herein that is equivalent to about 133 mg of bupivacaine. In some embodiments, the $C_{max}$ occurs after about 48 hours following the administration of the multivesicular liposome composition to the subject. In some embodiments, the $C_{max}$ occurs after about 72 hours following the administration of the multivesicular liposome composition to the subject.

In some embodiments of the methods herein, the plasma $C_{max}$ of bupivacaine in the subject is about 300 ng/mL to about 550 ng/mL, such as about 350 ng/mL to about 500 ng/mL, such as about 450 mg/mL, such as about 460 ng/mL, for an amount of the pharmaceutical composition described herein that is equivalent to about 266 mg of bupivacaine. In some embodiments, the $C_{max}$ occurs after about 48 hours following the administration of the multivesicular liposome composition to the subject. In some embodiments, the $C_{max}$ occurs after about 72 hours following the administration of the multivesicular liposome composition to the subject.

In some embodiments of the methods herein, the plasma $C_{max}$ of bupivacaine in the subject is less than about 850 ng/mL, such as less than about 800 ng/mL, such as less than about 750 ng/mL, such as less than about 700 ng/mL, such as less than about 650 ng/mL, such as less than about 600 ng/mL.

In some embodiments of the methods herein, the plasma $C_{max}$ of bupivacaine in a pediatric subject aged 6 to <12 years following spine surgery is about 250 ng/mL to about 440 ng/mL, such as about 320 ng/mL, In some embodiments of the methods herein, the plasma $C_{max}$ of bupivacaine in a pediatric subject aged 12 to <17 years following spine surgery is about 200 ng/mL to about 600 ng/mL, such as about 225 ng/mL to about 400 ng/mL, such as about 246 ng/mL to about 296 ng/mL), In some embodiments of the methods herein, the plasma $C_{max}$ of bupivacaine in a pediatric subject aged 6 to <12 years following cardiac surgery is about 250 ng/mL to about 1300 ng/mL, such as about 275 ng/mL to about 500 ng/mL, such as about 300 ng/mL to about 450 ng/mL), such as about 307 ng/mL to about 320 ng/mL), In some embodiments, a plasma $T_{max}$ of bupivacaine in a pediatric subject aged 12 to <17 years is about 1.1 hours following administration of the pharmaceutical composition to the subject.

In some embodiments, a plasma $T_{max}$ of bupivacaine in a pediatric subject aged 12 to <17 years is about 18.0 hours following administration of the pharmaceutical composition to the subject.

In some embodiments, a first plasma $T_{max}$ of bupivacaine in a pediatric subject aged 12 to <17 years is about 1.1 hours following administration of the pharmaceutical composition to the subject and a second plasma $T_{max}$ of bupivacaine is about 18.0 hours following administration of the pharmaceutical composition to the subject.

In some embodiments, a plasma $T_{max}$ of bupivacaine in a pediatric subject aged 6 to <12 years who is undergoing or has undergone spine surgery is about 2.4 hours following administration of the pharmaceutical composition to the subject.

In some embodiments, a plasma $T_{max}$ of bupivacaine in a pediatric subject aged 6 to <12 years who is undergoing or has undergone spine surgery is about 15.3 hours following administration of the pharmaceutical composition to the subject.

In some embodiments, a first plasma $T_{max}$ of bupivacaine in a pediatric subject aged 6 to <12 years who is undergoing or has undergone spine surgery is about 2.4 hours following administration of the pharmaceutical composition to the subject and a second plasma $T_{max}$ of bupivacaine is about 15.3 hours following administration of the pharmaceutical composition to the subject.

In some embodiments, a plasma $T_{max}$ of bupivacaine in a pediatric subject aged 6 to <12 years who is undergoing or has undergone cardiac surgery is about 0.4 hours following administration of the pharmaceutical composition to the subject.

In some embodiments, a plasma $T_{max}$ of bupivacaine in a pediatric subject aged 6 to <12 years who is undergoing or has undergone cardiac surgery is about 30.1 hours following administration of the pharmaceutical composition to the subject.

In some embodiments, a first plasma $T_{max}$ of bupivacaine in a pediatric subject aged 6 to <12 years who is undergoing or has undergone cardiac surgery is about 0.4 hours following administration of the pharmaceutical composition to the subject and a second plasma $T_{max}$ of bupivacaine is about 30.1 hours following administration of the pharmaceutical composition to the subject.

In some embodiments of the methods herein, the apparent elimination half-life of bupivacaine in the subject is from about 4 hours to about 50 hours, such as from about 4 hours to about 48 hours, such as from about 5 hours to about 45 hours, such as from about 15 hours to about 35 hours, such as from about 24.9 hours to 26.8 hours.

In some embodiments, the pharmaceutical composition comprising bupivacaine, wherein the composition does not comprise an opioid, is administered with a non-opioid analgesic. In some embodiments, the non-opioid analgesic is an NSAID.

In some embodiments, the pharmaceutical composition comprising bupivacaine, wherein the composition does not comprise an opioid, is a multivesicular liposomal particle pharmaceutical composition.

In some embodiments, the multivesicular liposomal particle pharmaceutical composition comprising bupivacaine, wherein the composition does not comprise an opioid, is administered with a non-opioid analgesic. In some embodiments, the non-opioid analgesic is an NSAID.

In some embodiments, the subject is a human.

In some embodiments of the method of treating pain in a pediatric subject, wherein the subject is a first subject, in the first about 72 hours following administration of the pharmaceutical composition to the first subject the opioid is administered to the first subject in a total amount that is lower than the total amount of an opioid that is administered to a second pediatric subject in the first about 72 hours following administration to the second subject of non-liposomal bupivacaine containing the same amount of bupivacaine as the pharmaceutical composition, wherein a pharmaceutical composition comprising: a) a multivesicular liposome comprising: at least one amphipathic lipid, and at least one neutral lipid; and b) an aqueous phase comprising: at least one polyhydroxy carboxylic acid and at least one dior tri-protic mineral acid; and bupivacaine phosphate, wherein the aqueous phase is encapsulated within the multivesicular liposome, is not administered to the second subject.

In some embodiments of the method of treating pain in a pediatric subject, wherein the subject is a first subject, in the first about 72 hours following administration of the pharmaceutical composition to the first subject the opioid is administered to the first subject in a total amount that is lower than the total amount of an opioid that is administered to a second pediatric subject in the first about 72 hours following administration to the second subject of non-liposomal bupivacaine containing the same amount of bupivacaine as the pharmaceutical composition, wherein a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome, is not administered to the second subject.

In some embodiments of the method of treating pain in a pediatric subject, wherein the subject is a first subject, in the first about 72 hours following administration of the pharmaceutical composition to the first subject the opioid is administered to the first subject in a total amount that is lower than the total amount of an opioid that is administered to a second pediatric subject in the first about 72 hours following administration to the second subject of non-liposomal bupivacaine containing the same amount of bupivacaine as the pharmaceutical composition, wherein a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate,
is not administered to the second subject.

In some embodiments of the method of treating pain in a pediatric subject, wherein the subject is a first subject, in the first about 72 hours following administration of the pharmaceutical composition to the first subject the opioid is administered to the first subject in a total amount that is lower than the total amount of an opioid that is administered to a second pediatric subject in the first about 72 hours following administration to the second subject of non-liposomal bupivacaine containing the same amount of bupivacaine as the pharmaceutical composition, wherein a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, is not administered to the second subject.

In some embodiments of the method of treating pain in a pediatric subject, wherein the subject is a first subject, in the first about 72 hours following administration of the pharmaceutical composition to the first subject the opioid is administered to the first subject in a total amount that is lower than the total amount of an opioid that is administered to a second pediatric subject in the first about 72 hours following administration to the second subject of non-liposomal bupivacaine containing the same amount of bupivacaine as the pharmaceutical composition, wherein a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, is not administered to the second subject.

In some embodiments of the method of treating pain in a pediatric subject, wherein the subject is a first subject, in the first about 72 hours following administration of the pharmaceutical composition to the first subject the opioid is administered to the first subject in a total amount that is lower than the total amount of an opioid that is administered to a second pediatric subject in the first about 72 hours following administration to the second subject of non-liposomal bupivacaine containing the same amount of bupivacaine as the pharmaceutical composition, wherein a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, is not administered to the second subject.

In some embodiments, the opioid that is administered to the first subject and the opioid that is administered to the second subject are the same. In some embodiments, the opioid that is administered to the first subject and the opioid that is administered to the second subject are different.

In some embodiments of the method of treating pain in a pediatric subject, wherein the subject is a first subject, in the first about 72 hours following administration of the pharmaceutical composition to the first subject, the opioid is administered to the first subject in a total amount that is lower than the total amount of an opioid that is administered to each of a plurality of second subjects in the first about 72 hours following respective administration to each of the second subjects of non-liposomal bupivacaine containing the same amount of bupivacaine as the pharmaceutical composition, wherein a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, is not administered to the second subjects.

In some embodiments of the method of treating pain in a pediatric subject, wherein the subject is a first subject, in the first about 72 hours following administration of the pharmaceutical composition to the first subject, the opioid is administered to the first subject in a total amount that is lower than the total amount of an opioid that is administered to each of a plurality of second subjects in the first about 72 hours following respective administration to each of the second subjects of non-liposomal bupivacaine containing the same amount of bupivacaine as the pharmaceutical composition, wherein a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome, is not administered to the second subjects.

In some embodiments of the method of treating pain in a pediatric subject, wherein the subject is a first subject, in the first about 72 hours following administration of the pharmaceutical composition to the first subject, the opioid is administered to the first subject in a total amount that is lower than the total amount of an opioid that is administered to each of a plurality of second subjects in the first about 72 hours following respective administration to each of the second subjects of non-liposomal bupivacaine containing the same amount of bupivacaine as the pharmaceutical composition, wherein a pharmaceutical composition comprising multivesicular liposomes encapsulating bupivacaine phosphate, said multivesicular liposomes comprising:

bupivacaine or a salt thereof;

phosphoric acid;

a lipid component comprising at least one amphipathic lipid and at least one neutral lipid lacking a hydrophilic head group; and, optionally, a cholesterol and/or a plant sterol wherein said multivesicular liposomes are made by a process comprising:

a) preparing a first aqueous component comprising phosphoric acid;

preparing a lipid component comprising at least one organic solvent, at least one amphipathic lipid, and at least one neutral lipid lacking a hydrophilic head group;

mixing said first aqueous component and said lipid component to form a water-in-oil emulsion, wherein at least one component comprises bupivacaine or a salt thereof;

d) mixing said water-in-oil emulsion with a second aqueous component to form solvent spherules; and removing the organic solvent from the solvent spherules to form multivesicular liposomes encapsulating bupivacaine phosphate, not administered to the second subjects.

some embodiments of the method of treating pain in a pediatric subject, wherein the subject is a first subject, in the first about 72 hours following administration of the pharmaceutical composition to the first subject, the opioid is administered to the first subject in a total amount that is lower than the total amount of an opioid that is administered to each of a plurality of second subjects in the first about 72 hours following respective administration to each of the second subjects of non-liposomal bupivacaine containing the same amount of bupivacaine as the pharmaceutical composition, wherein a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, is not administered to the second subjects.

some embodiments of the method of treating pain in a pediatric subject, wherein the subject is a first subject, in the first about 72 hours following administration of the pharmaceutical composition to the first subject, the opioid is administered to the first subject in a total amount that is lower than the total amount of an opioid that is administered to each of a plurality of second subjects in the first about 72 hours following respective administration to each of the second subjects of non-liposomal bupivacaine containing the same amount of bupivacaine as the pharmaceutical composition, wherein a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, not administered to the second subjects.

some embodiments of the method of treating pain in a pediatric subject, wherein the subject is a first subject, in the first about 72 hours following administration of the pharmaceutical composition to the first subject, the opioid is administered to the first subject in a total amount that is lower than the total amount of an opioid that is administered to each of a plurality of second subjects in the first about 72 hours following respective administration to each of the second subjects of non-liposomal bupivacaine containing the same amount of bupivacaine as the pharmaceutical composition, wherein a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, rein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, not administered to the second subjects.

some embodiments, the opioid that is administered to the first subject and the opioid that is administered to at least one of the second subjects are the same. In some embodiments, the opioid that is administered to the first subject and the opioid that is administered to at least one of the second subjects are different. In some embodiments, the opioid that is administered to the first subject and the opioids that are administered to the second subjects are the same. In some embodiments, the opioid that is administered to the first subject and the opioids that are administered to the second subjects are different. In some embodiments, the total amount of an opioid that is administered to each of a plurality of second subjects is a mean total amount.

some embodiments of the methods herein, the opioid is administered to the first subject in a total amount that is at least about 20% lower, such as at least about 30% lower, such as at least about 40% lower, such as at least about 50% lower than the total amount of the opioid that is administered to the second subject. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 72 hours following administration of the pharmaceutical composition to the first subject the opioid is administered to the first subject in a total amount that is at least about 20% lower, such as at least about 30% lower, such as at least about 40% lower, such as at least about 50% lower than the total amount of the opioid that is administered to the second subject in the first about 72 hours following administration to the second subject of non-liposomal bupivacaine. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 24 hours following administration of the pharmaceutical composition to the first subject the opioid is administered to the first subject in a total amount that is lower than the total amount of the opioid that is administered to the second subject in the first about 24 hours following administration to the second subject of non-liposomal bupivacaine. In some embodiments of the methods herein, in the first about 24 hours following administration of the pharmaceutical composition to the first subject the opioid is administered to the first subject in a total amount that is at least about 20% lower, such as at least about 30% lower, such as at least about 40% lower, such as at least about 50% lower than the total amount of the opioid that is administered to the second subject in the first about 24 hours administration to the second subject of non-liposomal bupivacaine. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 48 hours following administration of the pharmaceutical composition to the first subject the opioid is administered to the first subject in a total amount that is lower than the total amount of the opioid that is administered to the second subject in the first about 48 hours following administration to the second subject of non-liposomal bupivacaine. In some embodiments of the methods herein, in the first about 48 hours following administration of the pharmaceutical composition to the first subject the opioid is administered to the first subject in a total amount that is at least about 20% lower, such as at least about 30% lower, such as at least about 40% lower, such as at least about 50% lower than the total amount of the opioid that is administered to the second subject in the first about 48 hours following administration to the second subject of non-liposomal bupivacaine. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 7 days following administration of the pharmaceutical composition to the first subject the opioid is administered to the first subject in a total amount that is lower than the total amount of the opioid that is administered to the second subject in the first about 7 days following administration to the second subject of non-liposomal bupivacaine. In some embodiments of the methods herein, in the first about 7 days following administration of the pharmaceutical composition to the first subject the opioid is administered to the first subject in a total amount that is at least about 20% lower, such as at least about 30% lower, such as at least about 40% lower, such as at least about 50% lower than the total amount of the opioid that is administered to the second subject in the first about 7 days following administration to the second subject of non-liposomal bupivacaine. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 14 days following administration of the pharmaceutical composition to the first subject the opioid is administered to the first subject in a total amount that is lower than the total amount of the opioid that is administered to the second subject in the first about 14 days following administration to the second subject of non-liposomal bupivacaine. In some embodiments of the methods herein, in the first about 14 days following administration of the pharmaceutical composition to the first subject the opioid is administered to the first subject in a total amount that is at least about 20% lower, such as at least about 30% lower, such as at least about 40% lower, such as at least about 50% lower than the total amount of the opioid that is administered to the second subject in the first about 14 days following administration to the second subject of non-liposomal bupivacaine. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, the first subject has a pruritus score as determined by the 5-D itch scale that is lower than the pruritus score for the second subject.

In some embodiments of the methods herein, the plasma $AUC_{0-\infty}$, value of bupivacaine in the first subject following administration of the pharmaceutical composition to the first subject is at least about 120% higher, such as at least about 130% higher, such as at least about 140% higher, such as 150% higher than the plasma $AUC_{0-\infty}$, value of bupivacaine in the second subject following administration to the second subject of non-liposomal bupivacaine in an amount equivalent to half of the amount of bupivacaine administered to the first subject.

In some embodiments, the method does not comprise administering an analgesic, such as an opioid, to the subject following the administration of the pharmaceutical composition to the subject.

In some embodiments, the method does not comprise administering one or more morphinans to the subject following the administration of the pharmaceutical composition to the subject. In some embodiments, the method does not comprise administering morphine to the subject following the administration of the pharmaceutical composition to the subject.

In some embodiments, the method does not comprise administering an opioid to the first subject following the administration of the pharmaceutical composition to the subject.

In some embodiments, the method does not comprise administering one or more morphinans to the first subject. In some embodiments, the method does not comprise administering morphine to the first subject.

In some embodiments, the first subject is a human and the second subject is a human.

In some embodiments, the method comprises administering to the subject an amount of a pharmaceutical composition described herein that is equivalent to about 10 to about 300 mg of bupivacaine. In some embodiments the pharmaceutical composition comprises an amount equivalent to from about 10 mg to about 300 mg of bupivacaine. In some embodiments the pharmaceutical composition comprises an amount equivalent to from about 133 mg to about 266 mg of bupivacaine. In some embodiments the pharmaceutical composition comprises an amount equivalent to from about 10 mg to about 70 mg of bupivacaine. In some embodiments the pharmaceutical composition comprises an amount equivalent to from about 20 mg to about 60 mg of bupivacaine. In some embodiments the pharmaceutical composition comprises an amount equivalent to from about 20 mg to about 50 mg of bupivacaine. In some embodiments the pharmaceutical composition comprises an amount equivalent to from about 20 mg to about 40 mg of bupivacaine. In some embodiments the pharmaceutical composition comprises an amount equivalent to from about 20 mg to about 30 mg of bupivacaine. In some embodiments the pharmaceutical composition comprises an amount equivalent to from about 30 mg to about 60 mg of bupivacaine. In some embodiments the pharmaceutical composition comprises an amount equivalent to from about 30 mg to about 50 mg of bupivacaine. In some embodiments the pharmaceutical composition comprises an amount equivalent to from about 30 mg to about 40 mg of bupivacaine. In some embodiments the amount of the pharmaceutical composition described herein is equivalent to from about 10 mg to about 70 mg of bupivacaine. In some embodiments the amount of the pharmaceutical composition described herein is equivalent to from about 10 mg to about 60 mg of bupivacaine. In some embodiments the amount of the pharmaceutical composition described herein is equivalent to from about 20 mg to about 60 mg of bupivacaine. In some embodiments the amount of the pharmaceutical composition described herein is equivalent to from about 20 mg to about 50 mg of bupivacaine. In some embodiments the amount of the pharmaceutical composition described herein is equivalent to from about 20 mg to about 40 mg of bupivacaine. In some embodiments the amount of the pharmaceutical composition described herein is equivalent to from about 20 mg to about 30 mg of bupivacaine. In some embodiments the amount of the pharmaceutical composition described herein is equivalent to from about 30 mg to about 60 mg of bupivacaine. In some embodiments the amount of the pharmaceutical composition described herein is equivalent to from about 30 mg to about 50 mg of bupivacaine. In some embodiments the amount of the pharmaceutical composition described herein is equivalent to from about 30 mg to about 40 mg of bupivacaine.

In some embodiments the amount of the pharmaceutical composition described herein is equivalent to 13.3 mg of bupivacaine. In some embodiments the amount of the pharmaceutical composition described herein is equivalent to 26.6 mg of bupivacaine. In some embodiments the amount of the pharmaceutical composition described herein is equivalent to 39.9 mg of bupivacaine. In some embodiments the amount of the pharmaceutical composition described herein is equivalent to 53.2 mg of bupivacaine.

In some embodiments, the method comprises administering one or more non-opioid analgesics to the subject. In some embodiments, the one or more non-opioid analgesics are one or more NSAIDs. In some embodiments, the one or more non-opioid analgesics are one or more of ketorolac, acetaminophen or ibuprofen. Thus, in some embodiments, the method comprises administering one or more of ketorolac, acetaminophen or ibuprofen to the subject, wherein the one or more of ketorolac, acetaminophen or ibuprofen, is administered to the subject for up to 72 hours following the administration of the pharmaceutical composition to the subject in the following amounts:

IV ketorolac 15 mg once at the time of skin incision closure and prior to the TAP infiltration
    Intravenous (IV) acetaminophen 1000 mcg at the time of skin incision closure
    Scheduled oral (PO) acetaminophen 650 mg at the end of surgery and every 6 hours (q6h) for up to 72 hours
    Scheduled PO ibuprofen 600 mg at the end of surgery and q6h for up to 72 hours In some embodiments, the method comprises administering an opioid to a subject following the administration of the pharmaceutical composition to the subject, wherein one or more opioids are administered in the following amounts:

oral immediate-release oxycodone at 5-10 mg every 4 hours or as needed
    IV morphine at 1-2 mg or hydromorphone initiated at 0.3-0.5 mg every 4 hours or as needed In some embodiments, administering to the subject the pharmaceutical composition disclosed herein provides a $T_{max}$ of bupivacaine in plasma that is higher than the $T_{max}$ of bupivacaine in plasma provided by the injection of non-liposomal bupivacaine containing the same amount of bupivacaine as the pharmaceutical composition disclosed herein into the subject.

In some embodiments, administering to the subject the pharmaceutical composition disclosed herein provides a $T_{max}$ of bupivacaine in plasma that is higher than the $T_{max}$ of bupivacaine in plasma provided by the injection of non-liposomal bupivacaine containing an amount of bupivacaine that is equivalent to one half of the amount of bupivacaine in the pharmaceutical composition disclosed herein into the subject.

In some embodiments, administering to the subject the pharmaceutical composition disclosed herein provides a $C_{max}$ of bupivacaine in plasma that is lower than the $C_{max}$ of bupivacaine in plasma provided by the injection of non-liposomal bupivacaine containing the same amount of bupivacaine as the pharmaceutical composition disclosed herein into the subject.

In some embodiments, administering to the subject the pharmaceutical composition disclosed herein provides an apparent terminal elimination half-life (t ½el) of bupivacaine in plasma that is higher than the t ½el of bupivacaine in plasma provided by the injection of non-liposomal bupivacaine containing the same amount of bupivacaine as the pharmaceutical composition disclosed herein into the subject.

In some embodiments, administering to the subject the pharmaceutical composition disclosed herein provides an apparent elimination half-life (t½) of bupivacaine in plasma that is higher than the t½ of bupivacaine in plasma provided by the injection of non-liposomal bupivacaine containing the same amount of bupivacaine as the pharmaceutical composition disclosed herein into the subject.

In some embodiments, administering to the subject the pharmaceutical composition disclosed herein provides an apparent terminal elimination half-life (t½) of bupivacaine in plasma that is higher than the t ½el of bupivacaine in plasma provided by the injection of non-liposomal bupivacaine containing an amount of bupivacaine that is equivalent to one half of the amount of bupivacaine in the pharmaceutical composition pharmaceutical composition disclosed herein into the subject.

In some embodiments, administering to the subject the pharmaceutical composition disclosed herein provides an apparent elimination half-life (t½) of bupivacaine in plasma that is higher than the t½ of bupivacaine in plasma provided by the injection of non-liposomal bupivacaine containing an amount of bupivacaine that is equivalent to one half of the amount of bupivacaine in the pharmaceutical composition pharmaceutical composition disclosed herein into the subject.

In some embodiments, administering to the subject the pharmaceutical composition induces an onset of motor block in the subject after a shorter period of time than is provided by the injection of non-liposomal bupivacaine containing the same amount of bupivacaine as the pharmaceutical composition disclosed herein into the subject.

In some embodiments, duration of motor block in the subject is shorter than duration of motor block in the subject when non-liposomal bupivacaine containing the same amount of bupivacaine as the pharmaceutical composition disclosed herein is administered to the subject.

In some embodiments, to test onset and duration of motor effects, the following assessments are performed:
Handheld dynamometer
Bromage scale
Berg balance scale (7 item)

Thus, in some aspects of embodiments herein, the onset of the motor block is determined with a handheld dynamometer. In some aspects of embodiments herein, the onset of the motor block is determined according to the Bromage scale. In some aspects of embodiments herein, the onset of the motor block is determined according to the Berg balance scale.

Thus, in some aspects of embodiments herein, the duration of the motor block is determined with a handheld dynamometer. In some aspects of embodiments herein, the duration of the motor block is determined according to the Bromage scale. In some aspects of embodiments herein, the duration of the motor block is determined according to the Berg balance scale.

In some embodiments, onset and offset of motor block are evaluated using a handheld dynamometer at knee extension. In some embodiments, onset of motor block is defined as the earliest time point after injection into the subject of the pharmaceutical composition when a 20% or greater weakness from baseline is noted. In some embodiments offset of motor block is defined as the earliest time point after onset of motor block when less than 20% weakness from baseline is noted. Duration of motor block is the time between onset and offset of motor block.

In some embodiments, administering to the subject the pharmaceutical composition induces an onset of sensory block in the subject after a longer period of time than is provided by the injection of non-liposomal bupivacaine containing the same amount of bupivacaine as the pharmaceutical composition disclosed herein into the subject.

In some embodiments, duration of sensory block in the subject is longer than duration of sensory block in the subject when non-liposomal bupivacaine containing the same amount of bupivacaine as the pharmaceutical composition disclosed herein is administered to the subject.

In some embodiments, onset and segmental spread of sensory block are evaluated by testing the sensitivity to pinprick and cold in the S1, L2, L3, L4, T10-11, T7-8, and T4 dermatomes. In some embodiments, onset of sensory block is the earliest time point after injection into the subject of the pharmaceutical composition at which loss of sensation is noted below L2, such as S1, L3 and/or L4. In some embodiments, offset of sensory block will be defined as the earliest time point after onset of block at which recovery of sensation at L4 and S1 is noted.

Duration of sensory block is the time between onset and offset of sensory block.

Thus, in some aspects of embodiments herein, the onset of the sensory block is determined by testing the sensitivity to pinprick in one or more of the S1, L2, L3, L4, T10-11, T7-8, and T4 dermatomes, such as, for example, the S1, L3 and L4 dermatomes. In some aspects of embodiments herein, the onset of the sensory block is determined by testing the sensitivity to cold in one or more of the S1, L2, L3, L4, T10-11, T7-8, and T4 dermatomes, such as, for example, the S1, L3 and L4 dermatomes.

Thus, in some aspects of embodiments herein, the offset of the sensory block is determined by testing recovery of sensation in one or more of the S1, L2, L3, L4, T10-11, T7-8, and T4 dermatomes, such as, for example, the S1, L3 and L4 dermatomes.

In some embodiments, the administration of the pharmaceutical composition to the subject is performed in a manner analogous to that described in Zel et al., *British Journal of Anaesthesia*, 122(3): 1e9 (2018), accepted Oct. 19, 2019, doi: 10.1016/j.bja.2018.10.025, incorporated by reference herein in its entirety.

In some embodiments of any of the methods disclosed herein, the method produces postsurgical local analgesia.

In some embodiments of any of the methods disclosed herein, the method produces postsurgical regional analgesia.

In some embodiments of any of the methods disclosed herein, the subject does not experience neurological side effects.

In some embodiments of any of the methods disclosed herein, the subject does not experience cardiac side effects.

Unless otherwise defined, all technical and scientific terms used herein have the same meaning as commonly understood by one of ordinary skill in the art to which this invention belongs. Although methods and materials similar to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

The term "therapeutically effective" as it pertains to bupivacaine or a salt thereof, such as bupivacaine phosphate, present in the pharmaceutical compositions described herein, means that an anesthetic present in the first aqueous phase within the multivesicular liposome is released in a manner sufficient to achieve a particular level of anesthesia. Exact dosages will vary depending on such factors as the particular anesthetic, as well as patient factors such as age, sex, general condition, and the like. Those of skill in the art can readily take these factors into account and use them to establish effective therapeutic concentrations without resort to undue experimentation.

As used herein, "non-liposomal bupivacaine" refers to bupivacaine that is not in liposomal form. For example, "non-liposomal bupivacaine" refers to bupivacaine that is not comprised in a multivesicular liposome. The term "non-liposomal bupivacaine" also encompasses a composition comprising bupivacaine that is not in liposomal form.

As used herein, a "VAS pain intensity score" refers to the Visual Analog Scale pain intensity score described in Delgado et al., *J Am Acad Orthop Surg Glob Res Rev.* 2018 March; 2(3): e088 published online 2018 March 23. doi: 10.5435/JAAOSGlobal-D-17-00088, incorporated by reference herein in its entirety.

In some embodiments the compositions used in the methods disclosed herein comprise a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments the compositions used in the methods disclosed herein comprise: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments the compositions used in the methods disclosed herein comprise multivesicular liposomes encapsulating bupivacaine phosphate, said multivesicular liposomes comprising:
- bupivacaine or a salt thereof;
- phosphoric acid;
- a lipid component comprising at least one amphipathic lipid and at least one neutral lipid lacking a hydrophilic head group; and,
- optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments the compositions used in the methods disclosed herein are multivesicular liposomal particle pharmaceutical compositions made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein the compositions used in the methods disclosed herein are compositions of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein the compositions used in the methods disclosed herein are compositions comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments the aqueous phase further comprises hydrochloric acid.

Multivesicular liposomes (or "MVL", which is used herein to refer to a multivesicular liposome or a plurality of multivesicular liposomes) are lipid vesicles having multiple non-concentric internal aqueous chambers having internal membranes distributed as a network throughout the MVL. The chambers may contain acids which are effective to enable the encapsulation of bupivacaine or a salt thereof and to modulate its release rate. A preparation of MVL is described, for example, in Kim et al., Biochim. Biophys. Acta 728, 339-348, 1983. In some embodiments, a MVL is prepared in accordance with a process as described in U.S. Pat. No. 9,192,575, incorporated by reference herein in its entirety. In some embodiments, a MVL is prepared in accordance with a process as described in U.S. Pat. No. 8,182,835, incorporated by reference herein in its entirety. In some embodiments, a MVL is prepared in accordance with a process as described in U.S. Pat. No. 8,834,921, incorporated by reference herein in its entirety. In some embodiments, a MVL is prepared in accordance with a process as described in U.S. Pat. No. 9,205,052, incorporated by reference herein in its entirety.

In some embodiments the multivesicular liposomes ("MVL") are made by the following process. A "water-in-oil" type emulsion containing a non-hydrohalic acid salt of bupivacaine, such as bupivacaine phosphate, is formed from two immiscible phases, a lipid phase and a first aqueous phase. The lipid phase is made up of at least one amphipathic lipid and at least one neutral lipid in a volatile organic solvent. The term "amphipathic lipid" refers to molecules having a hydrophilic "head" group and a hydrophobic "tail" group and may have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capability by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

The amphipathic lipid is chosen from a wide range of lipids having a hydrophobic region and a hydrophilic region in the same molecule. Suitable amphipathic lipids are zwitterionic phospholipids, including phosphatidylcholines, phosphatidylethanolamines, sphingomyelins, lysophosphatidylcholines, and lysophosphatidylethanolamines. Also suitable are the anionic amphipathic phospholipids such as phosphatidylglycerols, phosphatidylserines, phosphatidylinositols, phosphatidic acids, and cardiolipins. Also suitable are the cationic amphipathic lipids such as acyl trimethylammonium propanes, diacyl dimethylammonium propanes, and stearylamines.

Suitable neutral lipids are triglycerides, propylene glycol esters, ethylene glycol esters, and squalene. Examples of triglycerides useful in the present invention are triolein, tripalmitolein, trimyristolein, trilinolein, tributyrin, tricaproin, tricaprylin, and tricaprin. The fatty chains in the triglycerides useful in the present invention can be all the same, or not all the same (mixed chain triglycerides), including all different. Both saturated and unsaturated fatty chains are useful in the present invention. The propylene glycol esters can be mixed diesters of caprylic and capric acids.

Many types of volatile organic solvents can be used in the present invention, including ethers, esters, halogenated ethers, hydrocarbons, halohydrocarbons, or Freons. For example, diethyl ether, chloroform, tetrahydrofuran, ethyl acetate, Forane, and any combinations thereof are suitable for use in making the compositions of the present invention.

Optionally, other components are included in the lipid phase. Among these are cholesterol or plant sterols.

The first aqueous phase includes bupivacaine or a salt thereof, such as bupivacaine phosphate, at least one polyhydroxy carboxylic acid, and at least one di- or tri-protic mineral acid. In some embodiments, also included is hydrochloric acid. The di- or tri-protic mineral acids include sulfuric acid, and phosphoric acid. Also included in the first aqueous phase are such polyhydroxy carboxylic acids as glucuronic acid, gluconic acid, and tartaric acid. The di- and tri-protic mineral acids and the polyhydroxy organic acids are present in the first aqueous phase in concentrations of from 0.01 mM to about 0.5 M, or preferably from about 5 mM to about 300 mM. When hydrochloric acid is used, it is present in lower amounts, from about 0.1 mM to about 50 mM, or preferably from about 0.5 mM to about 25 mM.

The lipid phase and first aqueous phase are mixed by mechanical turbulence, such as through use of rotating or vibrating blades, shaking, extrusion through baffled structures or porous pipes, by ultrasound, or by nozzle atomization, to produce a water-in-oil emulsion. Thus, bupivacaine or a salt thereof, such as bupivacaine phosphate, is encapsulated directly in the first step of MVL manufacture.

The whole water-in-oil emulsion is then dispersed into a second aqueous phase by means described above, to form solvent spherules suspended in the second aqueous phase. The term "solvent spherules" refers to a microscopic spheroid droplet of organic solvent, within which are suspended multiple smaller droplets of aqueous solution. The resulting solvent spherules therefore contain multiple aqueous droplets with the bupivacaine or a salt thereof, such as bupivacaine phosphate, dissolved therein. The second aqueous phase can contain additional components such as glucose, and/or lysine.

The volatile organic solvent is then removed from the spherules, for instance by surface evaporation from the suspension: When the solvent is substantially or completely evaporated, MVL are formed. Gases which can be used for the evaporation include nitrogen, argon, helium, oxygen, hydrogen, and carbon dioxide. Alternatively, the volatile solvent can be removed by sparging, rotary evaporation, or with the use of solvent selective membranes.

In some embodiments, an MVL is prepared in accordance with a process as described in U.S. Pat. No. 10,398,648, incorporated by reference herein in its entirety. In some embodiments, a MVL is prepared in accordance with a process as described in U.S. Pat. No. 9,585,838 incorporated by reference herein in its entirety.

In some embodiments, a MVL is prepared in accordance with a process as described in US 2011-0250264, US 2013-0306759, US 2013-0177634, US 2013-0177633, US 2013-0177635, US 2013-0195965, US 2013-0177636, US 2013-0183373, US 2013-0177638, US 2013-0177637, US 2013-0183372, US 2013-0183375, US 2016-0361260 or US 2018-0092847, each of which is incorporated by reference herein in its entirety.

Also included each in its entirety are the following references:

1. Li M M, Ocay D D, Teles A R, et al. Acute postoperative opioid consumption trajectories and long-term outcomes in pediatric patients after spine surgery. J Pain Res. 2019; 12:1673-1684.
2. Rabbitts J A, Groenewald C B, Tai G G, Palermo T M. Presurgical psychosocial predictors of acute postsurgical pain and quality of life in children undergoing major surgery. J Pain. 2015; 16(3):226-234.
3. Rabbitts J A, Zhou C, Groenewald C B, Durkin L, Palermo T M. Trajectories of postsurgical pain in children: risk factors and impact of late pain recovery on long-term health outcomes after major surgery. Pain. 2015; 156(11):2383-2389.
4. American Society of Anesthesiologists Task Force on Acute Pain M. Practice guidelines for acute pain management in the perioperative setting: an updated report by the American Society of Anesthesiologists Task Force on Acute Pain Management. Anesthesiology. 2012; 116(2): 248-273.
5. Gan T J. Poorly controlled postoperative pain: prevalence, consequences, and prevention. J Pain Res. 2017; 10:2287-2298.

6. Bigeleisen P E, Goehner N. Novel approaches in pain management in cardiac surgery. Curr Opin Anaesthesiol. 2015; 28(1):89-94.
7. Gerbershagen H J, Aduckathil S, van Wijck A J, Peelen L M, Kalkman C J, Meissner W. Pain intensity on the first day after surgery: a prospective cohort study comparing 179 surgical procedures. Anesthesiology. 2013; 118(4): 934-944.
8. Gottschalk A, Freitag M, Tank S, et al. Quality of postoperative pain using an intraoperatively placed epidural catheter after major lumbar spinal surgery. Anesthesiology. 2004; 101(1):175-180.
9. Shah S A, Guidry R, Kumar A, White T, King A, Heffernan M J. Current Trends in Pediatric Spine Deformity Surgery: Multimodal Pain Management and Rapid Recovery. Global Spine J. 2020; 10(3): 346-352.
10. Naropin [package insert]. Schaumberg, IL.: APP Pharmaceuticals, Inc.; 2010.
11. Marcaine [package insert]. Lake Forest, IL.: Hospira, Inc.; 2011.
12. Oda Y. Pharmacokinetics and systemic toxicity of local anesthetics in children. Journal of anesthesia. 2016; 30(4): 547-550.
13. Walker B J, Long J B, Sathyamoorthy M, et al. Complications in Pediatric Regional Anesthesia: An Analysis of More than 100,000 Blocks from the Pediatric Regional Anesthesia Network. Anesthesiology. 2018; 129(4):721-732.
14. EXPAREL [package insert]. San Diego, CA: Pacira Biosciences, Inc.; 2018.
15. Manna S, Wu Y, Wang Y, et al. Probing the mechanism of bupivacaine drug release from multivesicular liposomes. J Control Release. 2019; 294:279-287.
16. Chughtai M, Sultan A A, Hudson B, et al. Liposomal Bupivacaine Is Both Safe and Effective in Controlling Postoperative Pain After Spinal Surgery in Children: A Controlled Cohort Study. Clin Spine Surg. 2020.
17. Cohen B, Glosser L, Saab R, et al. Incidence of adverse events attributable to bupivacaine liposome injectable suspension or plain bupivacaine for postoperative pain in pediatric surgical patients: A retrospective matched cohort analysis. Paediatr Anaesth. 2019; 29(2): 169-174.
18. Day K M, Nair N M, Griner D, Sargent L A. Extended Release Liposomal Bupivacaine Injection (Exparel) for Early Postoperative Pain Control Following Pharyngoplasty. J Craniofac Surg. 2018; 29(3):726-730.
19. Hu D, Onel E, Singla N, Kramer W G, Hadzic A. Pharmacokinetic profile of liposome bupivacaine injection following a single administration at the surgical site. Clin Drug Investig. 2013; 33(2):109-115.
20. Patel M A, Gadsden J C, Nedeljkovic S S, et al. Brachial Plexus Block with Liposomal Bupivacaine for Shoulder Surgery Improves Analgesia and Reduces Opioid Consumption: Results from a Multicenter, Randomized, Double-Blind, Controlled Trial. Pain Med. 2020; 21(2): 387-400.
21. Rice D, Heil J W, Biernat L. Pharmacokinetic Profile and Tolerability of Liposomal Bupivacaine Following a Repeated Dose via Local Subcutaneous Infiltration in Healthy Volunteers. Clin Drug Investig. 2017; 37(3):249-257.
22. Springer B D, Mason J B, Odum S M. Systemic Safety of Liposomal Bupivacaine in Simultaneous Bilateral Total Knee Arthroplasty. J Arthroplasty. 2018; 33(1):97-101.
23. Ecoffey C. Refresher course: Local anesthetic pharmacology in children. Regional Anesthesia and Pain Medicine. 2015; 40(5):e23-e25.
24. Mazoit J X, Denson D D, Samii K. Pharmacokinetics of bupivacaine following caudal anesthesia in infants. Anesthesiology. 1988; 68(3):387-391.
25. Administration. USFaD. Pediatric Study Plans: Content of and Process for Submitting Initial Pediatric Study Plans and Ameded Initial Pediatric Study Plans Guidance for Industry. Retrieved from: https://www.fda.gov/media/86340/download. 2016.
26. American Society of Anesthesiologists. ASA Physical Status Classification System. Retrieved from: https://www.asahq.org/standards-and-guidelines/as a-physical-status-classification-system.
27. Tirotta C F, Munro H M, Salvaggio J, et al. Continuous incisional infusion of local anesthetic in pediatric patients following open heart surgery. Paediatr Anaesth. 2009; 19(6):571-576.

EXAMPLES

Example 1—Clinical Trial

Methods: A multicenter, open-label, phase 3, randomized trial (PLAY; NCT03682302) was conducted, with primary and secondary objectives evaluating the pharmacokinetics and safety, respectively, of multivesicular liposomal bupivacaine (EXPAREL®) in pediatric patients (age group 1: 12 to <17 years; age group 2: 6 to <12 years). The hypothesis was that the pharmacokinetics and safety profiles would support the safety of EXPAREL® (also referred to herein as "multivesicular liposomal bupivacaine" or "liposomal bupivacaine") in pediatric patients. Age group 1 received 4 mg/kg liposomal bupivacaine or 2 mg/kg bupivacaine hydrochloride (HCl) at the end of spine surgery; all patients in age group 2 received liposomal bupivacaine (4 mg/kg) at the end of spine or cardiac surgery. Surgeons administered treatments via local infiltration.

Results: Baseline characteristics were comparable across groups. Maximum plasma concentration ($C_{max}$) after liposomal bupivacaine administration was lower versus bupivacaine HCl in age group 1 (357 vs 564 ng/mL); mean $C_{max}$ in age group 2 was 320 and 447 ng/mL for cardiac and spine surgery, respectively. Median time to $C_{max}$ of liposomal bupivacaine occurred later with cardiac surgery versus spine surgery (22.7 vs 7.4 hours). In age group 1, the incidence of treatment-emergent adverse events (TEAEs) was comparable between liposomal bupivacaine (61% [n=31]) and bupivacaine HCl (73% [n=30]). In age group 2, 100% and 31% of patients undergoing spine (n=5) and cardiac (n=9) surgery experienced TEAEs, respectively. TEAEs were generally mild or moderate, with no discontinuations due to TEAEs or deaths. Conclusions: Plasma bupivacaine levels following local infiltration with liposomal bupivacaine remained below the toxic threshold in adults (2000-4000 ng/mL) across age groups and procedures. TEAEs were mild to moderate, supporting the safety of liposomal bupivacaine in pediatric patients undergoing spine or cardiac surgery.

Study Design

An open-label, randomized trial was conducted across 15 sites in the United States to evaluate the PK and safety of liposomal bupivacaine in pediatric patients aged 6 to 17 years undergoing spine or cardiac surgery. Each study site received institutional review board approval that complied with the International Conference on Harmonisation Good Clinical Practice and/or the United States Food and Drug Administration (FDA) Title 21 Code of Federal Regulations Part 56. Written informed consent was obtained for each patient or, if applicable, their parents or guardian. There were no protocol amendments.

This study was performed in 2 parts. Part 1 evaluated PK and safety of liposomal bupivacaine. Part 2 followed part 1 and further evaluated the safety of liposomal bupivacaine. For both parts of the study, pediatric patients aged 12 to <17 years (age group 1) were analyzed separately from patients aged 6 to <12 years (age group 2), per FDA guidance for safety studies in pediatric patients.[25]

Patient Eligibility

Investigators enrolled eligible pediatric patients who were scheduled to undergo spine (6 to <17 years of age) or cardiac (6 to <12 years of age) surgery, had body mass index within 5th to 95th percentile for age and sex, and were classified as ASA physical status of I, II, or 111.[26] Patients were excluded if they were pregnant, had history of hypersensitivity or idiosyncratic reactions to amide-type local anesthetics or opioids, had a contraindication to bupivacaine HCl, received liposomal bupivacaine or bupivacaine HCl within the past 30 days, had coagulopathies or immunodeficiency disorders, had history of drug or alcohol abuse in the past 2 years, had a clinically significant medical or psychiatric disease, or received an investigational drug within 30 days (or 5 elimination half-lives). Additionally, if patients experienced a clinically significant event or if a condition was uncovered during surgery that might have rendered the patient medically unstable (eg, excessive bleeding, acute sepsis), they did not receive liposomal bupivacaine or bupivacaine HCl.

Procedures and Treatment Groups

In age group 1, eligible pediatric patients aged 12 to <17 years undergoing spine surgery were randomized 1:1 to receive a single dose of either liposomal bupivacaine (4 mg/kg up to 266 mg) diluted with normal saline, or bupivacaine HCl (2 mg/kg up to 175 mg) via local infiltration at the end of surgery. Randomization was performed with a centralized randomization system using a unique subject identifier and unique random code identifier. In age group 2, all eligible pediatric patients aged 6 to <12 years of age undergoing either spine or cardiac surgery received liposomal bupivacaine (4 mg/kg up to 266 mg) via local infiltration at the end of surgery. Dosing for both age groups was weight based. Guidelines and training were shared with the participating surgeons to ensure reliability in infiltration techniques.

Across age groups and surgical procedures, surgeons administered liposomal bupivacaine or bupivacaine HCl via local infiltration prior to wound closure, with liposomal bupivacaine and bupivacaine HCl administered in small increments into the deep and superficial layers along the entire length of the incision site to ensure uniform drug distribution. Use of intraoperative opioids, acetaminophen, or other nonsteroidal anti-inflammatory drugs as well as postsurgical pain medication in cases of insufficient analgesia during and after surgery was permitted in accordance with the standard of care at each site. Use of local anesthetics within 96 hours after administration of liposomal bupivacaine was prohibited.

Endpoints and Assessments

The primary objective was to analyze PK of liposomal bupivacaine, including area under the plasma concentration-time curve (AUC), maximum plasma concentration ($C_{max}$), time to $C_{max}$ ($T_{max}$), apparent elimination half-life (t1/2), apparent clearance (CL/F), and apparent volume of distribution (Vd/F). To assess plasma concentration of bupivacaine, 8 blood samples were collected up to 42-60 hours after spine surgery and up to 64-72 hours after cardiac surgery in each patient. For both procedures, the first 4 samples were collected ~15, ~30, ~45, and 60-75 minutes after liposomal bupivacaine administration. The last 4 samples were collected in time windows rather than precise time points. For spine surgery, sample windows were 2-3, 10-18, 24-36, and 42-60 hours after receiving liposomal bupivacaine or bupivacaine HCl. For cardiac surgery, sample windows were 15-25, 30-40, 45-55, and 64-72 hours after receiving liposomal bupivacaine. These time points were chosen to characterize the PK of immediate release of bupivacaine and its early peak for both procedures, while minimizing the number of blood draws from each patient.

The secondary outcome was to evaluate the safety of liposomal bupivacaine in pediatric patients. Safety assessments included adverse events (AEs) up to 30 days after surgery, neurologic assessment, clinical laboratory tests, and vital signs. AEs of special interest (AESIs) included cardiac AESIs (chest pain, abnormal heart rate, or shortness of breath requiring intervention) and neurologic AESIs (seizure, altered mental status, rigidity, dysarthria, tremors, tinnitus, visual disturbance, and severe or worsening dizziness). Dizziness, hyperesthesia, muscular twitching, or tingling that persisted beyond 72 hours after dose were also considered AESIs. An AE was considered a treatment-emergent AE (TEAE) if the date and time of onset was between the start time of liposomal bupivacaine or bupivacaine HCl administration and the final day 30 visit.

Statistical Analysis

The sample size was determined on the basis of the number of patients needed to characterize the PK profile of liposomal bupivacaine in pediatric patients per FDA requirements. Authorized staff or a designee obtained the randomization assignment once eligible patients were at the clinic site for surgery. Descriptive statistics (number, mean, standard deviation [SD], median, minimum, maximum) were calculated for continuous data; tabulations (number and percentage) were calculated for categorial data. PK analysis included pediatric patients who underwent surgery, received treatment, and provided at least 1 blood sample for quantifiable plasma concentration measurement. PK measures were assessed by noncompartmental analysis. A separate PK analysis was conducted using nonlinear mixed-effect modeling (population PK method) with the spine surgery cohorts combined. The safety analysis included pediatric patients who underwent surgery and received treatment. The incidence of patients reporting TEAEs was tabulated by the number and percentage of patients reporting the TEAE. All analyses and tabulations were performed using SAS, version 9.4; PK descriptive statistics were performed using Sigmastat and Microsoft Excel.

Results

Patient Cohorts and Disposition

Patients Aged 12 to <17 Years (Age Group 1)

The PK analysis (part 1 of this study) included 31 patients undergoing spine surgery (liposomal bupivacaine, n=16; bupivacaine HCl, n=15). Safety analysis (parts 1 and 2 of this study) included 61 patients undergoing spine surgery (liposomal bupivacaine, n=31; bupivacaine HCl, n=30). There were 3 patients lost to follow-up (liposomal bupivacaine, n=1; bupivacaine HCl, n=2) (FIG. 1A). No blood samples were obtained after 1.25 hours for 1 patient, who was excluded from the liposomal bupivacaine arm.

Patients Aged 6 to <12 Years (Age Group 2)

The PK analysis (part 1) included 23 patients all receiving liposomal bupivacaine and undergoing either spine or cardiac surgery (spine surgery, n=2; cardiac surgery, n=21). The safety analysis (parts 1 and 2) included 34 patients all receiving liposomal bupivacaine and undergoing either spine or cardiac surgery (spine surgery, n=5; cardiac surgery, n=29). There were 3 discontinuations, including discontinuation due to an AE during surgery (spine surgery), not receiving liposomal bupivacaine at the chest incision site (cardiac surgery), and loss to follow-up (cardiac surgery; FIG. 1B).

Baseline, Demographic, and Surgery Characteristics

Patients Aged 12 to <17 Years (Age Group 1)

Baseline characteristics and demographics were generally comparable between treatment arms (Table 1). The mean (SD) incision length was comparable between treatment arms (liposomal bupivacaine, 30.9 [5.7] cm; bupivacaine HCl, 30.3 [4.1] cm).

Patients Aged 6 to <12 Years (Age Group 2)

Patients undergoing spine or cardiac surgery had comparable demographics and characteristics, although patients undergoing cardiac surgery had higher ASA physical status (93% ASA physical status III) compared with patients undergoing spine surgery (40% ASA physical status III) (Table 1). Patients undergoing spine surgery had a longer mean (SD) incision length (19.3 [13.6] cm) compared with patients undergoing cardiac surgery (13.0 [3.7] cm).

PK Analysis

Patients Aged 12 to <17 Years (Age Group 1)

Figure 2:
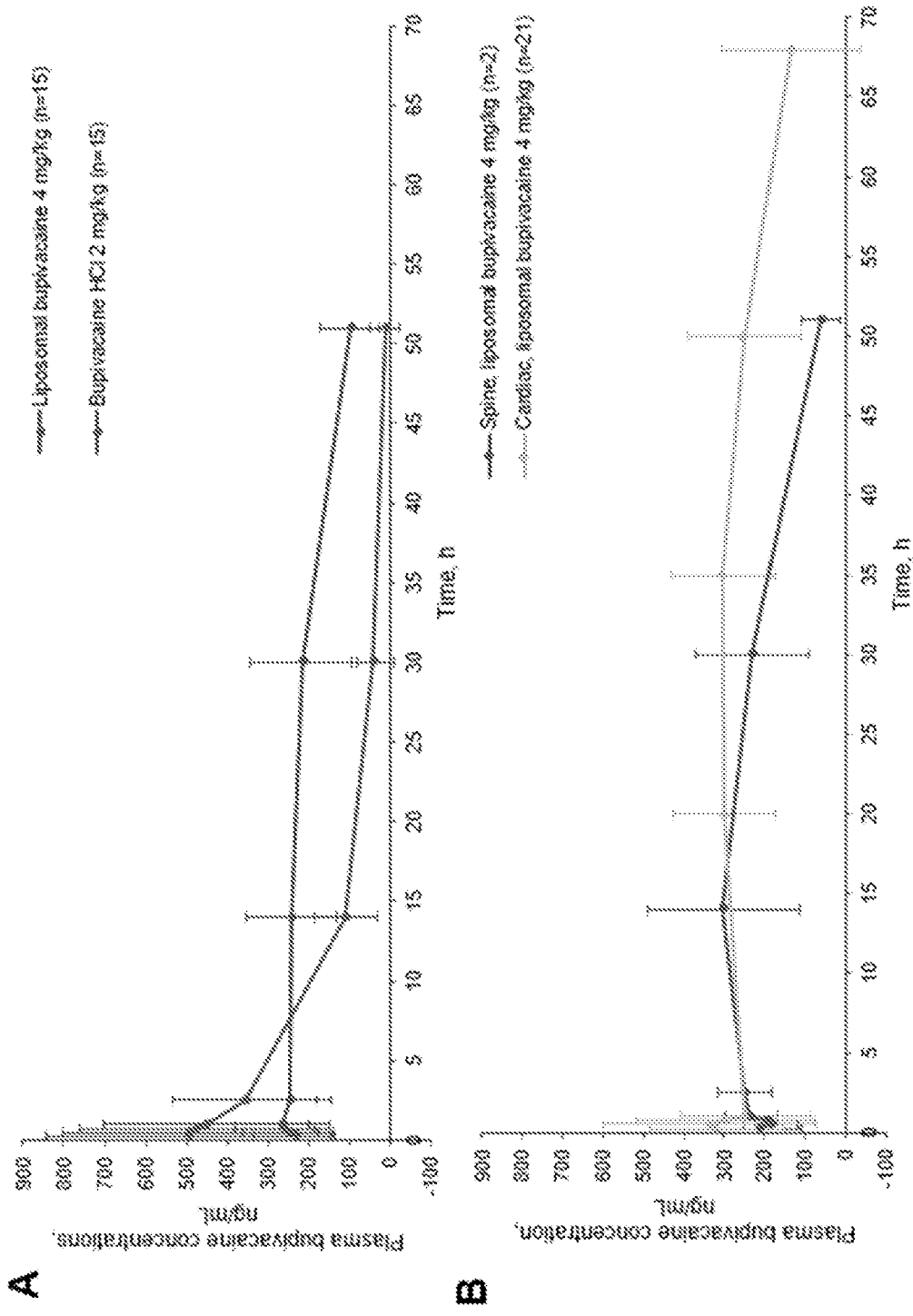
FIG. 2 shows the mean plasma bupivacaine concentration versus time profiles for age group 1 (A) and age group 2 (B). The last 4 samples were plotted in the midpoints of the time windows when they were collected (sample windows for spine surgery: 2-3 hours, 10-18 hours, 24-36 hours, and 42-60 hours after receiving liposomal bupivacaine or bupivacaine HCl; sample windows for cardiac surgery: 15-25 hours, 30-40 hours, 45-55 hours, and 64-72 hours after receiving liposomal bupivacaine or bupivacaine HCl). Error bars are the standard deviation. HCl, hydrochloride.
Figure 3:
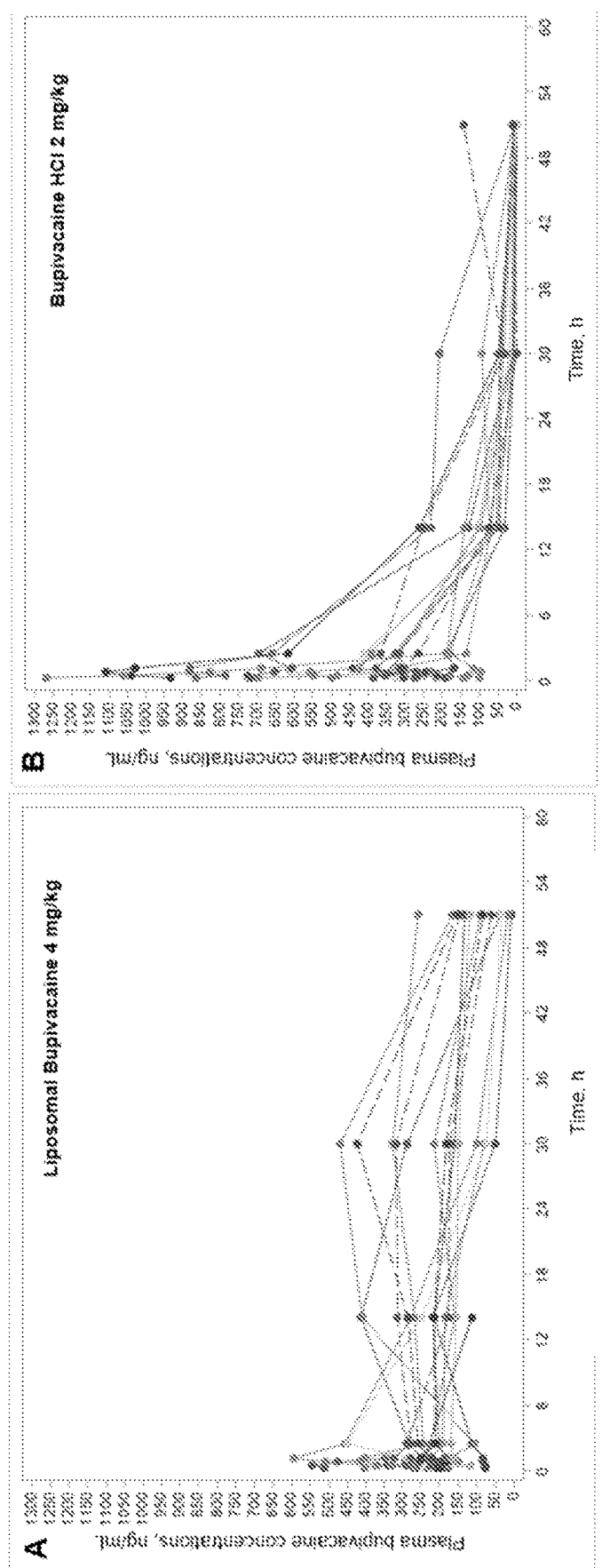
FIG. 3 shows individual plasma bupivacaine concentration versus time curves for patients in age group 1 receiving liposomal bupivacaine 4 mg/kg (A) or bupivacaine HCl 2 mg/kg (B) for spine surgery. HCl, hydrochloride.

Using noncompartmental analysis, administration of liposomal bupivacaine resulted in more sustained plasma bupivacaine concentrations, as well as higher AUC from start of dosing extrapolated to infinity ($AUC_{0-\infty}$), compared with bupivacaine HCl; the geometric mean $C_{max}$ was ~1.5-fold higher with bupivacaine HCl treatment than with liposomal bupivacaine (Table 2; FIG. 2A). For both treatments, overall $T_{max}$ occurred approximately 1 hour after administration; however, the distribution for liposomal bupivacaine was biphasic, with the initial $T_{max}$ at 1.1 hours after administration and the second $T_{max}$ at 18.0 hours after administration. The geometric mean tuz was nearly 3-fold longer in the liposomal bupivacaine treatment arm compared with the bupivacaine HCl treatment arm, suggesting prolonged bupivacaine exposure after liposomal bupivacaine. CL/F was comparable between treatment arms, although Vd/F was ~2.4-fold higher in the liposomal bupivacaine arm. The highest individual bupivacaine concentrations measured in any patient were 595 ng/mL for liposomal bupivacaine and 1270 ng/mL for bupivacaine HCl (FIG. 3).

One patient in the bupivacaine HCl treatment arm accidentally received a 4 mg/kg instead of 2 mg/kg dose; however, the data for this patient were retained in the PK analysis because a complete sample of plasma concentrations was collected, none of the PK parameter values were outliers, and CL/F and Vd/F naturally accounted for dose.

Patients Aged 6 to <12 Years (Age Group 2)

Figure 4:
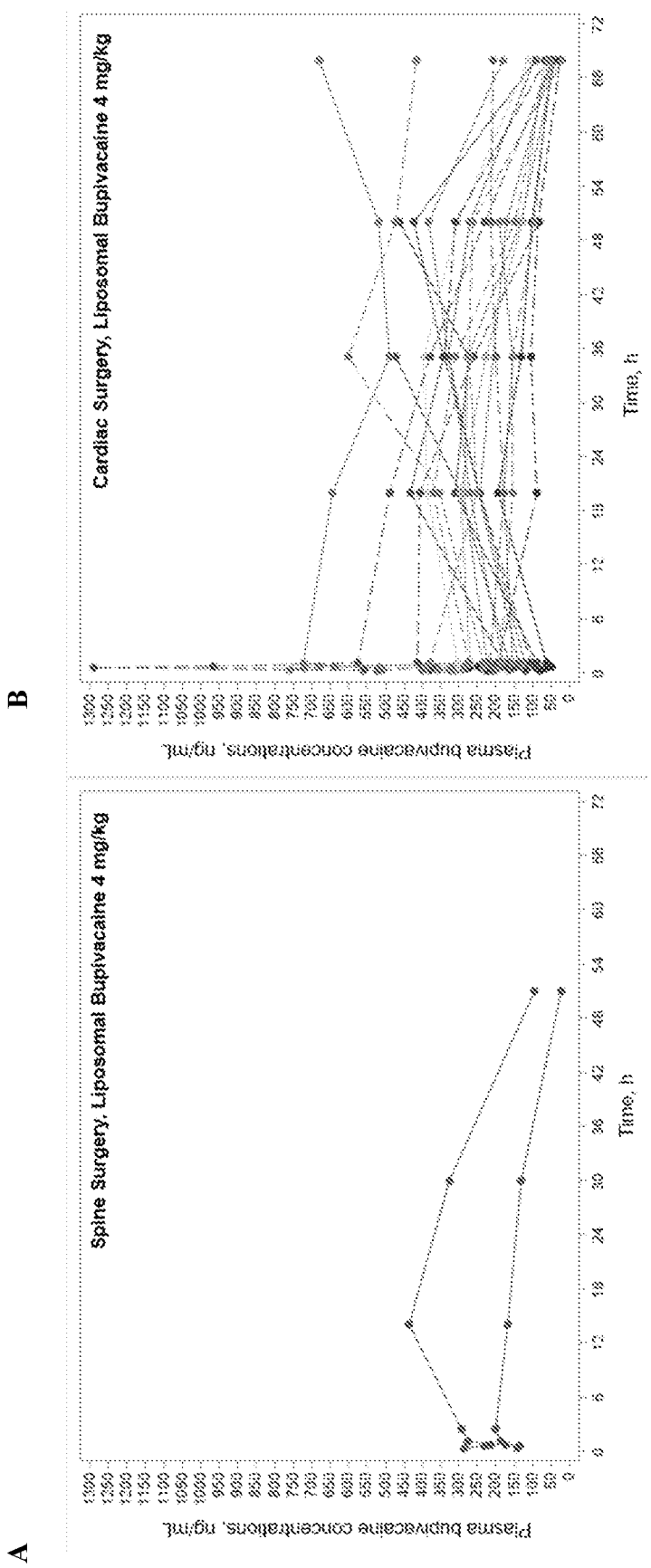
FIG. 4 shows individual plasma bupivacaine concentration versus time curves after liposomal bupivacaine 4 mg/kg for patients in age group 2 undergoing spine surgery (A) or cardiac surgery (B).

PK was assessed in only 2 patients in the spine surgery cohort; as such, geometric means were unable to be calculated. $C_{max}$ in age group 2 was generally comparable but slightly higher than the $C_{max}$ observed in older pediatric patients (age group 1), but differences were observed within age group 2 between the spine surgery and cardiac surgery cohorts (Table 2; FIG. 2B). Compared with patients undergoing spine surgery, $AUC_{0-\infty}$ was approximately double in patients undergoing cardiac surgery, which corresponded to CL/F values that were approximately half as high in the cardiac surgery cohort. The PK data suggested sustained bupivacaine concentrations after liposomal bupivacaine administration, with median $T_{max}$ occurring at 22.7 and 7.4 hours in patients undergoing cardiac surgery and spine surgery, respectively. Biphasic distribution of bupivacaine levels was also detected in this age group in both surgical procedures. The highest individual bupivacaine concentrations after liposomal bupivacaine administration measured in any patient were 436 ng/mL for spine surgery and 1290 ng/mL for cardiac surgery (FIG. 4).

Population PK Model

Across age groups, trends in PK parameters between liposomal bupivacaine and bupivacaine HCl using the population PK model were consistent with those observed with noncompartmental analysis (Table 4). The PK of bupivacaine in both age groups and surgery cohorts were adequately described by a linear 2-compartment PK model with fast and slow absorption routes for liposomal bupivacaine. For each treatment (liposomal bupivacaine or bupivacaine HCl), the $C_{max}$ in 12-year-old patients was predicted to be similar to that in 17-year-old patients in pediatric patients undergoing spine surgery. Median predicted early $T_{max}$ was comparable between patients receiving liposomal bupivacaine (50 minutes) and patients receiving bupivacaine HCl (40 minutes) for spine surgery; the predicted median early $T_{max}$ after liposomal bupivacaine in patients undergoing cardiac surgery was 20 minutes. Among patients receiving liposomal bupivacaine, the median late $T_{max}$ was predicted to occur at 15.8 and 23.2 hours for spine and cardiac surgery, respectively.

Safety

Patients Aged 12 to <17 Years (Age Group 1)

TEAEs were observed in 61% and 73% of patients who received liposomal bupivacaine 4 mg/kg and bupivacaine HCL 2 mg/kg, respectively (Table 3); there were no discontinuations due to TEAEs or on-study deaths for either treatment. The most common TEAEs were constipation, nausea, and vomiting. All TEAEs were mild to moderate in severity except for 1 severe TEAE (constipation) in a patient receiving bupivacaine HCl that was determined not to be treatment related. There were no serious TEAEs in the liposomal bupivacaine group.

There was a numerically higher incidence of treatment-related TEAEs after bupivacaine HCl (n=5; 16.7%) than after liposomal bupivacaine (n=2; 6.5%). Treatment-related TEAEs included nausea (liposomal bupivacaine, n=2; bupivacaine HCl, n=3), constipation (liposomal bupivacaine, n=1; bupivacaine HCl, n=3); vomiting (liposomal bupivacaine, n=1), vision blurred (liposomal bupivacaine, n=1), hypoesthesia (bupivacaine HCl, n=1), and paresthesia (bupivacaine HCl, n=1). Two patients (6.5%) and 3 patients (10%) experienced at least 1 AESI among patients receiving liposomal bupivacaine and bupivacaine HCl, respectively; no AESI was determined to be related to study treatment. AESIs included muscle twitching (liposomal bupivacaine, n=1; bupivacaine HCl, n=2), tachycardia (bupivacaine HCl, n=1), and dizziness (liposomal bupivacaine, n=1). No clinically meaningful differences in laboratory test results or vital signs were observed between study arms.

Patients Aged 6 to <12 Years (Age Group 2)

TEAEs were reported in 5 (100%) and 9 patients (31%) undergoing spine or cardiac surgery, respectively. All TEAEs were mild to moderate in severity, and no AESIs were reported. There were 3 patients with treatment-related TEAEs after spine surgery, and there were no treatment-related TEAEs after cardiac surgery. Three serious TEAEs occurred in 2 patients undergoing cardiac surgery (fungal wound infection and vomiting in 1 patient, and dyspnea in the other patient); these serious TEAEs were not considered treatment related and resolved.

There were 7 treatment-related TEAEs in 3 patients undergoing spine surgery including blurred vision (n=2), oral hypoesthesia (n=2), vomiting (n=1), nausea (n=1), and delayed recovery from anesthesia (n=1). No clinically meaningful differences in laboratory test results or vital signs were observed between surgery groups.

Discussion

This multicenter, open-label, phase 3, randomized trial (PLAY; NCT03682302) was conducted to evaluate the PK and safety of liposomal bupivacaine in pediatric patients undergoing spine or cardiac surgery. Local infiltration of a single dose of liposomal bupivacaine (4 mg/kg) at the end of spine surgery in patients aged 12 to <17 years resulted in prolonged plasma bupivacaine concentrations compared with local infiltration of bupivacaineHCl. Initial peak concentrations occurred at similar time points after liposomal bupivacaine and bupivacaine HCl administration (~1 hour after administration), with peak levels ~1.5-fold higher with bupivacaine HCl compared with liposomal bupivacaine. A second slight peak in plasma bupivacaine was observed ~18 hours after liposomal bupivacaine administration at the end of spine surgery that was not detected after bupivacaine HCl administration. Most TEAEs were mild or moderate, with few TEAEs related to liposomal bupivacaine. Collectively, these data support the safety of liposomal bupivacaine in pediatric patients aged 6 to <17 years undergoing spine or cardiac surgery.

Although the PK of levobupivacaine have been investigated in pediatric patients after administration of levobupivacaine via an elastomeric pump,[17] the PK of liposomal bupivacaine in a pediatric population have not been previously reported. The PK profiles after liposomal bupivacaine administration in the current study were comparable between age groups and were generally consistent with PK profiles of liposomal bupivacaine among adult patients.[19] For example, biphasic distribution of bupivacaine concentrations was observed after liposomal bupivacaine among pediatric patients after spine and cardiac surgery, with an initial peak ~1 hour after administration followed by a second peak 15-30 hours later, depending on age group and surgery type. A review of 4 clinical studies assessing PK profiles in male and female adults reported biphasic distribution of plasma bupivacaine levels after single administration of varying doses of liposomal bupivacaine (155-532 mg), with an initial peak occurring ~1 hour after administration followed by a second peak occurring ~12-36 hours later.[19] This biphasic pattern potentially reflects unique properties[15] of the liposomal formulation of bupivacaine, allowing for rapid uptake of bupivacaine initially followed by prolonged release of the anesthetic at the administration site. The geometric mean of both early and late $C_{max}$ after spine surgery in older pediatric patients (246 and 296 ng/mL, respectively) were comparable but slightly lower than early and late $C_{max}$ after cardiac surgery in younger pediatric patients (318 and 307 ng/mL, respectively), potentially conferring sustained analgesia beyond the initial hour after surgery.

Plasma bupivacaine concentrations after liposomal bupivacaine administration were higher and more sustained in patients undergoing cardiac surgery compared with patients undergoing spine surgery. Patients undergoing cardiac surgery also experienced a delayed time to $C_{max}$ versus patients undergoing spine surgery (22.7 vs 7.4 hours). This may be explained in part by differences in incision length: because local infiltration involves multiple injections over the length of the incision, the shorter incision length used during cardiac surgery may have concentrated liposomal bupivacaine in a small area, allowing for slower drug absorption, whereas the longer incision length used during spine surgery may have distributed liposomal bupivacaine over a greater area, allowing for more rapid drug absorption. These potential differences in surgical characteristics and PK should be considered when using liposomal bupivacaine.

The safety analysis revealed that most AEs were mild to moderate with a low incidence of serious AEs or treatment-related TEAEs. Comparable clearance rates between liposomal bupivacaine and bupivacaine HCl and only 1 case of delayed recovery after anesthesia suggest low likelihood of local anesthetic systemic toxicity with liposomal bupivacaine. Similarly, a prior retrospective review found no cases of local anesthetic systemic toxicity in 356 pediatric patients undergoing laparoscopic or open surgery who also received the same dose of liposomal bupivacaine via local wound infiltration as that used in the current study (4 mg/kg).[7] Mean and individual peak plasma bupivacaine concentrations after liposomal bupivacaine remained well below thresholds associated with neurotoxicity and cardiotoxicity in adult patients (~2000 to 4000 ng/mL) in both age cohorts after spine or cardiac surgery.[20-22] Although these threshold values were determined in adult patients and a toxicity threshold has not been formally established in pediatric patients, a toxicity threshold of 4000 ng/mL has been previously used to interpret PK data among pediatric patients undergoing cardiac surgery who received continuous local infusion of levobupivacaine.[27] Together, these results support a favorable safety profile of liposomal bupivacaine 4 mg/kg (up to 266 mg) administered via local infiltration in pediatric patients undergoing spine or cardiac surgery. A limitation to this study was the small sample size of patients aged 6 to <12 years undergoing spine surgery. This precluded the ability to compare PK values from this group with those in patients in this age group undergoing cardiac surgery or with older pediatric patients undergoing spine surgery.

In conclusion, the PK profiles of liposomal bupivacaine in pediatric patients aged 6 to <17 years are consistent with those in adult patients.[13] Most TEAEs were mild or moderate, with few cases of TEAEs related to liposomal bupivacaine and no serious TEAES related to liposomal bupivacaine use. Together, these data support the safety profile of liposomal bupivacaine for pediatric patients aged 6 to <17 years undergoing spine or cardiac surgery.

TABLE 1

Baseline Demographics and Characteristics (Safety Population)

|  | Age group 1 (12 to <17 years) | | | Age group 2 (6 to <12 years)[a] | | |
|---|---|---|---|---|---|---|
|  | Liposomal bupivacaine 4 mg/kg (n = 31) | Bupivacaine HCl 2 mg/kg (n = 30) | Total (n = 61) | Spine surgery (n = 5) | Cardiac surgery (n = 29) | Total (n = 34) |
| Age, mean (SD), y | 13.8 (1.3) | 13.9 (1.3) | 13.8 (1.3) | 10.0 (1.7) | 8.7 (1.8) | 8.9 (1.8) |
| Female, n (%) | 28 (90) | 22 (73) | 50 (82) | 2 (40) | 14 (48) | 16 (47) |
| Ethnicity, n (%) |  |  |  |  |  |  |
| Hispanic/Latino | 10 (32) | 7 (23) | 17 (28) | 0 (0) | 9 (31) | 9 (26) |
| Not Hispanic/Latino | 19 (61) | 23 (77) | 42 (69) | 5 (100) | 20 (69) | 25 (74) |
| Not reported | 2 (6) | 0 (0) | 2 (3) | 0 (0) | 0 (0) | 0 (0) |

TABLE 1-continued

Baseline Demographics and Characteristics (Safety Population)

| | Age group 1 (12 to <17 years) | | | Age group 2 (6 to <12 years)[a] | | |
|---|---|---|---|---|---|---|
| | Liposomal bupivacaine 4 mg/kg (n = 31) | Bupivacaine HCl 2 mg/kg (n = 30) | Total (n = 61) | Spine surgery (n = 5) | Cardiac surgery (n = 29) | Total (n = 34) |
| Race, n (%) | | | | | | |
| Asian | 2 (6) | 0 (0) | 2 (3) | 0 (0) | 0 | 0 (0) |
| Black/African American | 5 (16) | 3 (10) | 8 (13) | 1 (20) | 2 (7) | 3 (9) |
| White | 21 (68) | 26 (87) | 47 (77) | 4 (80) | 26 (90) | 30 (88) |
| Other | 1 (3) | 1 (3) | 2 (3) | 0 (0) | 0 (0) | 0 (0) |
| Not reported | 2 (6) | 0 (0) | 2 (3) | 0 (0) | 1 (3) | 1 (3) |
| ASA physical status, n (%) | | | | | | |
| I | 14 (45) | 13 (43) | 27 (44) | 1 (20) | 0 (0) | 1 (3) |
| II | 16 (52) | 13 (43) | 29 (48) | 2 (40) | 2 (7) | 4 (12) |
| III | 1 (3) | 4 (13) | 5 (8) | 2 (40) | 27 (93) | 29 (85) |
| Height, mean (SD), cm | 158.8 (13.6) | 160.9 (11.1) | 159.8 (12.4) | 141.5 (17.6) | 134.2 (13.0) | 135.2 (13.7) |
| Weight, mean (SD), kg | 53.4 (11.5) | 54.7 (13.4) | 54.0 (12.3) | 39.1 (14.7) | 34.9 (12.6) | 35.5 (12.7) |
| BMI, mean (SD), kg/m$^2$ | 21.0 (2.8) | 20.1 (3.9) | 21.0 (3.4) | 18.9 (3.0) | 18.9 (4.3) | 18.9 (4.1) |

[a]All patients in age group 2 received liposomal bupivacaine 4 mg/kg. ASA, American Society of Anesthesiologists; BMI, body mass index; HCl, hydrochloride; SD, standard deviation.

TABLE 2

Bupivacaine PK After Administration of Liposomal Bupivacaine or Bupivacaine HCl as Assessed by Noncompartmental Analysis (PK Pooulation)

| | Age group 1 (12 to <17 years) | | Age group 2 (6 to <12 years)[a] | |
|---|---|---|---|---|
| | Liposomal bupivacaine 4 mg/kg (n = 15)[b] | Bupivacaine HCl 2 mg/kg (n = 15) | Spine surgery (n = 2)[c] | Cardiac surgery (n = 21) |
| $AUC_{0-\infty}$, ng · h/mL | | | | |
| Mean (SD) | 14,246 (9119) | 5709 (3282) | 11,570 | 26,164 (28,038) |
| Geometric mean (% CV) | 12,257 (59) | 5064 (51) | — | 19,707 (75) |
| $C_{max}$, ng/mL | | | | |
| Mean (SD) | 357 (125) | 564 (321) | 320 | 447 (243) |
| Geometric mean (% CV) | 337 (37) | 488 (60) | — | 403 (46) |
| Early $C_{max}$, ng/mL | | | | |
| Mean (SD) | 322 (134) | — | 249 | 373 (271) |
| Geometric mean (% CV) | 296 (45) | — | — | 307 (69) |
| Late $C_{max}$, ng/mL | | | | |
| Mean (SD) | 264 (105) | — | 303 | 349 (145) |
| Geometric mean (% CV) | 246 (42) | — | — | 318 (48) |
| $t_{max}$, median (range), h | 1.1 (0.3-26.1) | 0.9 (0.3-2.5) | 7.4 | 22.7 (0.2-54.5) |
| Early $t_{max}$, median (range), h | 1.1 (0.3-2.7) | — | 2.4 | 0.4 (0.2-1.2) |
| Late $t_{max}$, median (range), h | 18.0 (11.1-26.1) | — | 15.3 | 30.1 (15.0-69.3) |
| $t_{1/2}$, h | | | | |
| Mean (SD) | 26.8 (21.3) | 8.4 (6.3) | 13.4 | 24.9 (20.6) |
| Geometric mean (% CV) | 21.2 (77) | 7.4 (48) | — | 20.5 (62) |
| CL/F, L/h | | | | |
| Mean (SD) | 17.5 (7.5) | 20.5 (8.3) | 14.5 | 7.4 (3.2) |
| Geometric mean (% CV) | 16.0 (48) | 18.9 (46) | — | 6.6 (58) |

TABLE 2-continued

Bupivacaine PK After Administration of Liposomal Bupivacaine or Bupivacaine HCl as Assessed by Noncompartmental Analysis (PK Pooulation)

|  | Age group 1 (12 to <17 years) | | Age group 2 (6 to <12 years)[a] | |
| --- | --- | --- | --- | --- |
|  | Liposomal bupivacaine 4 mg/kg (n = 15)[b] | Bupivacaine HCl 2 mg/kg (n = 15) | Spine surgery (n = 2)[c] | Cardiac surgery (n = 21) |
| Vd/F, L | | | | |
| Mean (SD) | 546 (269) | 227 (111) | 271 | 216 (84) |
| Geometric mean (% CV) | 488 (53) | 201 (57) | — | 197 (51) |

[a]All patients in age group 2 received liposomal bupivacaine 4 mg/kg.
[b]1 patient was excluded from all PK calculations because no blood samples were obtained from this patient after 1.25 hours.
[c]Geometric mean not calculated because only 2 patients underwent spine surgery in age group 2. % CV, percent coefficient of variation; $AUC_{0-\infty}$, area under the plasma concentration versus time curve from start of dosing extrapolated to infinity; CL/F, apparent clearance; $C_{max}$, maximum plasma concentration; HCl, hydrochloride; PK, pharmacokinetics; SD, standard deviation; $t_{1/2}$, apparent terminal elimination half-life; $t_{max}$, time to $C_{max}$; Vd/F, apparent volume of distribution.

TABLE 3

Overview of Treatment-Emergent Adverse Events (Safety Population)

|  | Age group 1 (12 to <17 years) | | Age group 2 (6 to <12 years)[a] | |
| --- | --- | --- | --- | --- |
|  | Liposomal bupivacaine 4 mg/kg (n = 31) | Bupivacaine HCl 2 mg/kg (n = 30) | Spine surgery (n = 5) | Cardiac surgery (n = 29) |
| Patients with any TEAE, n (%) | 19 (61) | 22 (73) | 5 (100) | 9 (31) |
| Maximum severity, n (%) | | | | |
| Mild | 12 (39) | 14 (47) | 3 (60) | 6 (21) |
| Moderate | 7 (22) | 7 (23) | 2 (40) | 3 (10) |
| Severe | 0 | 1 (3) | 0 | 0 |
| At least 1 treatment-related TEAE, n (%) | 2 (6) | 5 (17) | 3 (60) | 0 |
| At least 1 serious TEAE, n (%) | 0 | 0 | 0 | 2 (7) |
| At least 1 AESI, n (%) | 2 (6) | 3 (10) | 0 | 0 |
| Most common AEs (>10% in any category) | | | | |
| Constipation | 8 (26) | 9 (30) | 1 (20) | 4 (14) |
| Nausea | 10 (32) | 6 (21) | 1 (20) | 2 (7) |
| Vomiting | 9 (29) | 5 (17) | 1 (20) | 4 (14) |
| Diarrhea | 2 (6) | 0 | 1 (20) | 0 |
| Hypoesthesia oral | 1 (3) | 3 (10) | 3 (60) | 0 |
| Muscle twitching | 2 (6) | 8 (27) | 1 (20) | 1 (3) |
| Muscle spasms | 3 (10) | 0 | 1 (20) | 0 |
| Muscular weakness | 0 | 3 | — | — |
| Vision blurred | 4 (13) | 3 (10) | 3 (60) | 1 (3) |
| Hypotension | 2 (6) | 7 (23) | 2 (40) | 0 |
| Cardiac disorders | 2 (6) | 4 (13) | 1 (20) | 1 (3) |
| Bradycardia | 1 (3) | 0 | 1 (20) | 0 |
| Tachycardia | 1 (3) | 4 (13) | 0 | 1 (3) |
| Postsurgical anemia | 4 (13) | 0 | 1 (20) | 0 |
| Delayed recovery from anesthesia | 1 (3) | — | 1 (20) | 0 |
| Seroma | — | — | 1 (20) | 0 |
| Tachypnoea | 0 | 1 (3.3) | 1 (20) | 0 |
| Pruritus | 1 (3) | 2 (7) | 2 (40) | 0 |

[a]All patients in age group 2 received liposomal bupivacaine 4 mg/kg. AE, adverse event; AESI, AE of special interest; HCl, hydrochloride; TEAE, treatment-emergent AE.

TABLE 4

Bupivacaine Pharmacokinetics After Administration of Liposomal Bupivacaine or Bupivacaine HCl (Population PK Method)

| | Spine surgery (6 to <17 y), liposomal Bupivacaine 4 mg/kg (n = 18)[a] | Spine surgery (12 to <17 y), bupivacaine HCl 2 mg/kg (n = 15) | Cardiac surgery (6 to <12 y), liposomal bupivacaine 4 mg/kg (n = 21)[b] |
|---|---|---|---|
| Early $C_{max}$, ng/mL | 275 (34) | 444 (51) | 292 (57) |
| Late $C_{max}$, ng/mL[c] | 254 (36) | — | 311 (40) |
| $AUC_{0-\infty}$ (μg · h/mL) | 11.3 (45) | 6.4 (46) | 8.0 (56) |
| CL/F, L/h | 18.3 (34) | 16.8 (38) | 18.9 (37) |
| Vss/F, L | 125 (43) | 153 (49) | 91.6 (58) |
| $t_{1/2}$, h | 4.9 (55) | 6.5 (28) | 3.5 (64) |

Data are the geometric mean (% CV).
[a]Of 18 patients, 2 were aged 10 or 11 years and the remaining 16 were aged 12 to <17 years.
[b]One patient was 12 years of age.
[c]All patients in the bupivacaine HCl treatment arm were predicted to have only 1 peak. % CV, percent coefficient of variation; $AUC_{0-\infty}$, area under the plasma concentration versus time curve from start of dosing extrapolated to infinity; CL/F, apparent clearance; $C_{max}$, maximum plasma concentration; HCl, hydrochloride; $t_{1/2}$, apparent terminal elimination half-life; Vss/F, steady-state volume of distribution.

The invention claimed is:

1. A method of treating pain in a pediatric subject aged 12 to <17 years undergoing spine surgery, the method comprising:
    administering to the subject about 4 milligrams of a pharmaceutical composition per kilogram of the subject's body weight, the pharmaceutical composition comprising:
        a) a multivesicular liposome comprising: at least one amphipathic lipid, and at least one neutral lipid; and
        b) an aqueous phase comprising bupivacaine phosphate,
        wherein the aqueous phase is encapsulated within the multivesicular liposome.

2. The method of claim 1, wherein the pharmaceutical composition is administered by local infiltration prior to wound closure.

3. The method of claim 2, wherein the plasma Cmax of bupivacaine in the subject following spine surgery is about 225 ng/mL to about 400 ng/mL.

4. The method of claim 3, wherein the plasma Cmax of bupivacaine in the subject following spine surgery is about 246 ng/mL to about 296 ng/mL.

5. The method of claim 2, wherein the plasma Tmax of bupivacaine in the pediatric subject is about 1.1 hours following administration of the pharmaceutical composition to the subject.

6. The method of claim 5, wherein the plasma Tmax of bupivacaine in the pediatric subject is about 1.1 hours and about 18.0 hours following administration of the pharmaceutical composition to the subject.

7. The method of claim 1, wherein the pharmaceutical composition consists essentially of:
    a) a multivesicular liposome comprising: at least one amphipathic lipid, and at least one neutral lipid; and
    b) an aqueous phase consisting essentially of bupivacaine phosphate, wherein the aqueous phase is encapsulated within the multivesicular liposome.

8. A method of treating pain in a pediatric subject aged 6 to <12 years undergoing spine surgery, the method comprising:
    administering to the subject about 4 milligrams of a pharmaceutical composition per kilogram of the subject's body weight, the pharmaceutical composition comprising:
        a) a multivesicular liposome comprising: at least one amphipathic lipid, and at least one neutral lipid; and
        b) an aqueous phase comprising bupivacaine phosphate, wherein the aqueous phase is encapsulated within the multivesicular liposome.

9. The method of claim 8, wherein the pharmaceutical composition is administered by local infiltration prior to wound closure.

10. The method of claim 9, wherein the plasma Cmax of bupivacaine in the subject following spine surgery is about 250 ng/mL to about 440 ng/mL.

11. The method of claim 10, wherein the plasma Cmax of bupivacaine in the subject following spine surgery is 320 ng/mL.

12. The method of claim 8, wherein the Tmax of bupivacaine in the pediatric subject is about 2.4 hours following administration of the pharmaceutical composition to the subject.

13. The method of claim 11, wherein the Tmax of bupivacaine in the pediatric subject is about 2.4 hours and about 15.3 hours following administration of the pharmaceutical composition to the subject.

14. The method of claim 7, wherein the pharmaceutical composition consists essentially of:
    a) a multivesicular liposome comprising: at least one amphipathic lipid, and at least one neutral lipid; and
    b) an aqueous phase consisting essentially of bupivacaine phosphate, wherein the aqueous phase is encapsulated within the multivesicular liposome.

15. A method of treating pain in a pediatric subject aged 6 to <17 years undergoing cardiac surgery, the method comprising:
    administering to the subject about 4 milligrams of a pharmaceutical composition per kilogram of the subject's body weight, the pharmaceutical composition comprising:
        a) a multivesicular liposome comprising: at least one amphipathic lipid, and at least one neutral lipid; and
        b) an aqueous phase comprising bupivacaine phosphate, wherein the aqueous phase is encapsulated within the multivesicular liposome.

16. The method of claim 15, wherein the pharmaceutical composition is administered by local infiltration prior to wound closure.

17. The method of claim 16, wherein the pediatric subject is aged 6 to <12 years.

18. The method of claim 17, wherein the Cmax of bupivacaine in the subject following cardiac surgery is about 250 ng/mL to about 1300 ng/mL.

19. The method of claim 17, wherein the Tmax of bupivacaine in the pediatric subject is about 0.4 hours following administration of the pharmaceutical composition to the subject.

20. The method of claim 19, wherein the Tmax of bupivacaine in the pediatric subject is about 0.4 hours and about 30.1 hours following administration of the pharmaceutical composition to the subject.

21. The method of claim 16, wherein the pediatric subject is aged 12 to <17 years.

22. The method of claim 15, wherein the pharmaceutical composition consists essentially of:
    a) a multivesicular liposome comprising: at least one amphipathic lipid, and at least one neutral lipid; and
    b) an aqueous phase consisting essentially of bupivacaine phosphate, wherein the aqueous phase is encapsulated within the multivesicular liposome.

* * * * *